(12) United States Patent
Piippo Svendsen et al.

(10) Patent No.: US 11,806,041 B2
(45) Date of Patent: Nov. 7, 2023

(54) ATHERECTOMY DEVICES AND METHODS

(71) Applicant: Cardio Flow, Inc., St. Paul, MN (US)

(72) Inventors: Cassandra Ann Piippo Svendsen, Blaine, MN (US); Ryan D. Welty, Blaine, MN (US); Michael Kallok, St. Paul, MN (US)

(73) Assignee: Cardio Flow, Inc., St. Paul, MN (US)

( * ) Notice: Subject to any disclaimer, the term of this patent is extended or adjusted under 35 U.S.C. 154(b) by 44 days.

(21) Appl. No.: 18/150,369

(22) Filed: Jan. 5, 2023

(65) Prior Publication Data

US 2023/0149039 A1 May 18, 2023

Related U.S. Application Data

(63) Continuation of application No. 17/592,797, filed on Feb. 4, 2022, which is a continuation of application No. 16/530,284, filed on Aug. 2, 2019, now Pat. No. 11,272,954.

(60) Provisional application No. 62/715,643, filed on Aug. 7, 2018.

(51) Int. Cl.
*A61B 17/3207* (2006.01)
*A61B 17/32* (2006.01)
*A61B 17/22* (2006.01)

(52) U.S. Cl.
CPC ... *A61B 17/320758* (2013.01); *A61B 17/32002* (2013.01); *A61B 17/32075* (2013.01); *A61B 2017/22038* (2013.01); *A61B 2017/22094* (2013.01); *A61B 2017/320004* (2013.01); *A61B 2017/320741* (2013.01); *A61B 2017/320775* (2013.01)

(58) Field of Classification Search
CPC ..... A61B 17/320758; A61B 17/320766; A61B 17/32002; A61B 17/320725; A61B 2017/22038; A61B 2017/22094; A61B 2017/320004; A61B 2017/320775; A61B 2017/320766
See application file for complete search history.

(56) References Cited

U.S. PATENT DOCUMENTS

| | | |
|---|---|---|
| 1,431,416 A | 10/1922 | Parsons et al. |
| 1,916,085 A | 6/1933 | Summers et al. |
| 2,495,316 A | 6/1933 | Clark et al. |
| 3,929,129 A | 12/1975 | Archambault |
| 4,445,509 A | 5/1984 | Auth |
| 4,445,892 A | 5/1984 | Hussein et al. |

(Continued)

FOREIGN PATENT DOCUMENTS

| | | |
|---|---|---|
| CN | 104955406 A | 9/2015 |
| DE | 3105978 A1 | 12/1981 |

(Continued)

OTHER PUBLICATIONS

"Declaration of Dr. Morten Olgaard Jensen," IPIPR2018-01658, Exhibit 1002, dated Sep. 4, 2018.

(Continued)

*Primary Examiner* — Tuan V Nguyen
(74) *Attorney, Agent, or Firm* — Fish & Richardson P.C.

(57) ABSTRACT

Rotational atherectomy devices and systems can remove or reduce stenotic lesions in blood vessels by rotating one or more abrasive elements within the vessel. The abrasive elements are attached to a distal portion of an elongate flexible drive shaft that extends from a handle assembly that includes a driver for rotating the drive shaft. In particular implementations, the handle assembly encapsulates an electric motor assembly, a pump assembly, and a controller assembly.

19 Claims, 10 Drawing Sheets

(56) References Cited

U.S. PATENT DOCUMENTS

| | | |
|---|---|---|
| 4,620,320 A | 10/1986 | Sullivan |
| 4,646,736 A | 3/1987 | Auth |
| 4,762,130 A | 8/1988 | Fogarty et al. |
| 4,772,258 A | 9/1988 | Marangoni et al. |
| 4,784,636 A | 11/1988 | Rydell |
| 4,870,953 A | 10/1989 | DonMicheal et al. |
| 4,887,469 A | 12/1989 | Shoptaw |
| 4,931,635 A | 6/1990 | Toyama |
| 4,950,238 A | 8/1990 | Sullivan |
| 4,990,134 A | 2/1991 | Auth |
| 5,014,681 A | 5/1991 | Heeman et al. |
| 5,100,425 A | 3/1992 | Fischell et al. |
| 5,127,902 A | 7/1992 | Fischell |
| 5,181,920 A | 1/1993 | Mueller et al. |
| 5,213,576 A | 5/1993 | Abiuso et al. |
| 5,213,577 A | 5/1993 | Kratzer |
| 5,217,474 A | 6/1993 | Zacca et al. |
| 5,242,460 A | 9/1993 | Klein et al. |
| 5,250,059 A | 10/1993 | Andreas et al. |
| 5,250,060 A | 10/1993 | Carbo et al. |
| 5,273,526 A | 12/1993 | Dance et al. |
| 5,308,354 A | 5/1994 | Zacca et al. |
| 5,312,427 A | 5/1994 | Shturman |
| 5,314,407 A | 5/1994 | Auth et al. |
| 5,314,438 A | 5/1994 | Shturman |
| 5,342,292 A | 8/1994 | Nita et al. |
| 5,361,285 A | 11/1994 | Formanek |
| 5,370,653 A | 12/1994 | Cragg |
| 5,435,009 A | 7/1995 | Schild et al. |
| 5,458,575 A | 10/1995 | Wang |
| 5,556,389 A | 9/1996 | Liprie |
| 5,584,843 A | 12/1996 | Wulfman et al. |
| 5,649,941 A | 7/1997 | Lary |
| 5,667,490 A | 9/1997 | Keith et al. |
| 5,681,336 A | 10/1997 | Clement et al. |
| 5,730,717 A | 3/1998 | Gelbfish |
| 5,766,192 A | 6/1998 | Zacca |
| 5,771,895 A | 6/1998 | Slager |
| 5,816,923 A | 10/1998 | Milo et al. |
| 5,836,957 A | 11/1998 | Schulz et al. |
| 5,843,103 A | 12/1998 | Wulfman |
| 5,868,708 A | 2/1999 | Hart et al. |
| 5,893,857 A | 4/1999 | Shturman et al. |
| 5,897,566 A | 4/1999 | Shturman et al. |
| 6,001,112 A | 12/1999 | Taylor |
| 6,010,533 A | 1/2000 | Pope et al. |
| 6,015,420 A | 1/2000 | Wulfman et al. |
| 6,022,363 A | 2/2000 | Walker et al. |
| 6,024,749 A | 2/2000 | Shturman et al. |
| 6,030,401 A | 2/2000 | Marino |
| 6,039,747 A | 3/2000 | Shturman et al. |
| 6,066,152 A | 5/2000 | Strauss et al. |
| 6,077,282 A | 6/2000 | Shturman et al. |
| 6,096,054 A | 8/2000 | Wyzgala et al. |
| 6,132,444 A | 10/2000 | Shturman et al. |
| 6,135,982 A | 10/2000 | Campbell |
| 6,146,395 A | 11/2000 | Kanz et al. |
| 6,152,911 A | 11/2000 | Giannoble |
| 6,156,048 A | 12/2000 | Wulfman et al. |
| 6,217,595 B1 | 4/2001 | Shturman et al. |
| 6,241,706 B1 | 6/2001 | Leschinsky et al. |
| 6,270,465 B1 | 8/2001 | Keith et al. |
| 6,416,526 B1 | 7/2002 | Wyzgala et al. |
| 6,485,500 B1 | 11/2002 | Kokish et al. |
| 6,491,660 B2 | 12/2002 | Guo et al. |
| 6,494,890 B1 | 12/2002 | Shturman et al. |
| 6,497,711 B1 | 12/2002 | Plaia et al. |
| 6,565,588 B1 | 5/2003 | Clement et al. |
| 6,626,861 B1 | 9/2003 | Hart et al. |
| 6,685,718 B1 | 2/2004 | Wyzgala et al. |
| 6,733,513 B2 | 5/2004 | Boyle et al. |
| 6,805,485 B2 | 10/2004 | Hogan et al. |
| 6,818,001 B2 | 11/2004 | Wulfman et al. |
| 6,852,118 B2 | 2/2005 | Shturman et al. |
| 6,955,661 B1 | 10/2005 | Herweck et al. |
| 7,252,674 B2 | 8/2007 | Wyzgala et al. |
| 7,666,202 B2 | 2/2010 | Prudnikov et al. |
| 7,766,049 B2 | 8/2010 | Miller et al. |
| 8,109,954 B2 | 2/2012 | Shturman et al. |
| 8,109,955 B2 | 2/2012 | Shturman |
| 8,137,369 B2 | 3/2012 | Shturman |
| 8,142,458 B2 | 3/2012 | Shturman |
| 8,147,507 B2 | 4/2012 | Shturman |
| 8,157,825 B2 | 4/2012 | Shturman |
| 8,177,801 B2 | 5/2012 | Kallok et al. |
| 8,348,965 B2 | 1/2013 | Prudnikov et al. |
| 8,353,923 B2 | 1/2013 | Shturman |
| 8,388,636 B2 | 3/2013 | Shturman |
| 8,388,637 B2 | 3/2013 | Shturman |
| 8,454,638 B2 | 6/2013 | Shturman |
| 8,465,510 B2 | 6/2013 | Shturman |
| 8,496,678 B2 | 7/2013 | Shturman |
| 8,500,764 B2 | 8/2013 | Shturman |
| 8,500,765 B2 | 8/2013 | Shturman |
| 8,597,313 B2 | 12/2013 | Thatcher et al. |
| 8,628,550 B2 | 1/2014 | Narveson |
| 8,663,195 B2 | 3/2014 | Shturman |
| 8,663,260 B2 | 3/2014 | Shturman |
| 8,663,261 B2 | 3/2014 | Shturman |
| 8,936,589 B2 | 1/2015 | Shturman |
| 9,089,362 B2 | 7/2015 | Shturman |
| 9,192,405 B2 | 11/2015 | Shturman |
| 9,211,138 B2 | 12/2015 | Shturman |
| 9,237,903 B2 | 1/2016 | Shturman |
| 9,289,230 B2 | 3/2016 | Cambronne |
| 9,333,006 B2 | 5/2016 | Shturman |
| 9,364,256 B2 | 6/2016 | Shturman |
| 9,387,006 B2 | 7/2016 | Shturman |
| 9,597,109 B2 | 3/2017 | Shturman |
| 9,737,329 B2 | 8/2017 | Shturman |
| 9,757,144 B2 | 9/2017 | Shturman |
| 9,788,853 B2 | 10/2017 | Robinson et al. |
| 9,883,886 B2 | 2/2018 | Shturman |
| 10,052,122 B2 | 8/2018 | Higgins et al. |
| 10,052,124 B2 | 8/2018 | Cambronne |
| 10,064,646 B2 | 9/2018 | Cambronne |
| 10,226,276 B2 | 3/2019 | Kessler |
| 2002/0007190 A1 | 1/2002 | Wulfman et al. |
| 2002/0013600 A1 | 1/2002 | Scribner et al. |
| 2002/0029056 A1 | 3/2002 | Hall et al. |
| 2002/0082547 A1 | 6/2002 | Deniega et al. |
| 2002/0099367 A1 | 7/2002 | Guo et al. |
| 2002/0138088 A1 | 9/2002 | Nash et al. |
| 2002/0151918 A1 | 10/2002 | Lafontaine et al. |
| 2002/0165567 A1 | 11/2002 | Shiber |
| 2002/0188276 A1 | 12/2002 | Evans et al. |
| 2003/0078594 A1 | 4/2003 | Shturman et al. |
| 2003/0078606 A1 | 4/2003 | Lafontaine et al. |
| 2003/0114869 A1 | 6/2003 | Nash et al. |
| 2003/0120296 A1 | 6/2003 | Shturman et al. |
| 2003/0125756 A1 | 7/2003 | Shturman et al. |
| 2003/0139689 A1 | 7/2003 | Shturman et al. |
| 2003/0199889 A1 | 10/2003 | Kanz et al. |
| 2004/0098014 A1 | 5/2004 | Flugelman et al. |
| 2004/0158270 A1 | 8/2004 | Wyzgala et al. |
| 2005/0154416 A1 | 7/2005 | Herweck et al. |
| 2005/0209615 A1 | 9/2005 | Prudnikov et al. |
| 2005/0228402 A1 | 10/2005 | Hofmann |
| 2005/0240146 A1 | 10/2005 | Nash et al. |
| 2005/0245864 A1 | 11/2005 | O'Brien et al. |
| 2005/0256461 A1 | 11/2005 | DiFiore et al. |
| 2006/0189929 A1 | 8/2006 | Lary et al. |
| 2006/0258976 A1 | 11/2006 | Shturman et al. |
| 2007/0006690 A1 | 1/2007 | Foster |
| 2007/0007190 A1 | 1/2007 | Pethke |
| 2007/0066888 A1 | 3/2007 | Maschke |
| 2007/0239182 A1 | 10/2007 | Glines et al. |
| 2008/0097498 A1 | 4/2008 | Shimizu et al. |
| 2008/0161840 A1 | 7/2008 | Osiroff et al. |
| 2008/0306498 A1 | 12/2008 | Thatcher et al. |
| 2008/0319415 A1 | 12/2008 | Shturman |
| 2009/0018564 A1 | 1/2009 | Shturman |
| 2009/0069829 A1 | 3/2009 | Shturman |
| 2009/0105736 A1 | 4/2009 | Prudnikov et al. |
| 2009/0182359 A1 | 7/2009 | Shturman |
| 2009/0264908 A1 | 10/2009 | Kallok et al. |
| 2009/0312777 A1 | 12/2009 | Shturman |
| 2009/0318942 A1 | 12/2009 | Shturman |

(56) References Cited

U.S. PATENT DOCUMENTS

| | | |
|---|---|---|
| 2009/0326568 A1 | 12/2009 | Shturman |
| 2010/0010522 A1 | 1/2010 | Shturman |
| 2010/0049226 A1 | 2/2010 | Shturman |
| 2010/0121361 A1 | 5/2010 | Plowe et al. |
| 2010/0125276 A1 | 5/2010 | Palermo |
| 2010/0211088 A1 | 8/2010 | Narveson |
| 2011/0009888 A1 | 1/2011 | Shturman |
| 2011/0054332 A1 | 3/2011 | Shturman |
| 2011/0213391 A1 | 9/2011 | Rivers et al. |
| 2012/0035633 A1 | 2/2012 | Shturman et al. |
| 2012/0109170 A1 | 5/2012 | Shturman et al. |
| 2012/0150207 A1 | 6/2012 | Shturman |
| 2012/0157906 A1 | 6/2012 | Underwood et al. |
| 2012/0157907 A1 | 6/2012 | Underwood et al. |
| 2012/0172903 A1 | 7/2012 | Shturman |
| 2012/0178986 A1 | 7/2012 | Campbell et al. |
| 2012/0191113 A1 | 7/2012 | Shturman |
| 2012/0213391 A1 | 8/2012 | Usami et al. |
| 2012/0253186 A1* | 10/2012 | Simpson et al. ......... A61B 6/12 600/426 |
| 2013/0060270 A1 | 3/2013 | Teeslink et al. |
| 2013/0103062 A1 | 4/2013 | To et al. |
| 2013/0178881 A1 | 7/2013 | Shturman |
| 2013/0204280 A1 | 8/2013 | Shturman |
| 2013/0245654 A1 | 9/2013 | Shturman |
| 2013/0253552 A1* | 9/2013 | Schoenle et al. ......... A61B 17/320758 606/159 |
| 2013/0274773 A1 | 10/2013 | Shturman et al. |
| 2013/0296904 A1 | 11/2013 | Shturman |
| 2013/0296905 A1 | 11/2013 | Shturman |
| 2013/0310589 A1 | 11/2013 | Ripley et al. |
| 2013/0310859 A1 | 11/2013 | Shturman |
| 2013/0333365 A1 | 12/2013 | Silet et al. |
| 2014/0046243 A1* | 2/2014 | Ray et al. ......... A61B 17/22 604/22 |
| 2014/0081298 A1 | 3/2014 | Cambronne |
| 2014/0180317 A1 | 6/2014 | Shturman |
| 2014/0180318 A1 | 6/2014 | Shturman |
| 2014/0180319 A1 | 6/2014 | Shturman |
| 2014/0222042 A1 | 8/2014 | Kessler et al. |
| 2014/0277014 A1 | 9/2014 | Higgins et al. |
| 2014/0303551 A1 | 10/2014 | Germain et al. |
| 2014/0371770 A1 | 12/2014 | Schoenle et al. |
| 2015/0080795 A1 | 3/2015 | Mattison et al. |
| 2015/0094733 A1 | 4/2015 | Shiber |
| 2015/0164540 A1 | 6/2015 | Higgins et al. |
| 2015/0196320 A1 | 7/2015 | Robinson et al. |
| 2015/0201956 A1 | 7/2015 | Higgins et al. |
| 2016/0157886 A1 | 6/2016 | WasDyke et al. |
| 2016/0199093 A1 | 7/2016 | Cambronne et al. |
| 2016/0346003 A1 | 12/2016 | Grothe et al. |
| 2017/0056040 A1 | 3/2017 | Vetter et al. |
| 2017/0065396 A1 | 3/2017 | Look et al. |
| 2017/0290603 A1 | 10/2017 | Piippo Svendsen et al. |
| 2018/0064464 A1 | 3/2018 | Robinson et al. |
| 2018/0235652 A1 | 8/2018 | Benjamin et al. |
| 2018/0263654 A1 | 9/2018 | Steele et al. |
| 2019/0083126 A1 | 3/2019 | Benjamin et al. |
| 2019/0307483 A1* | 10/2019 | Flury et al. .... A61B 17/320758 |

FOREIGN PATENT DOCUMENTS

| | | |
|---|---|---|
| DE | 20305953 U1 | 8/2003 |
| EP | 0419154 A1 | 3/1991 |
| EP | 0479433 A2 | 4/1992 |
| EP | 0820729 A1 | 1/1998 |
| EP | 1405797 A2 | 4/2004 |
| EP | 1820458 A1 | 8/2007 |
| EP | 3105978 A1 | 12/2016 |
| FR | 1595757 A | 6/1970 |
| GB | 854573 A | 11/1960 |
| GB | 2039208 A | 8/1980 |
| GB | 2271060 A | 4/1994 |
| GB | 2357573 A | 6/2001 |
| GB | 2426458 A | 11/2006 |
| WO | 1997/14470 | 4/1997 |
| WO | 1998/50101 | 11/1998 |
| WO | 1999/44513 | 9/1999 |
| WO | 2001/15759 | 3/2001 |
| WO | 2002/09599 | 2/2002 |
| WO | 2003/061457 | 7/2003 |
| WO | 2006/126076 | 11/2006 |
| WO | 2006/126175 | 11/2006 |
| WO | 2006/126176 | 11/2006 |
| WO | 2008/006704 | 1/2008 |
| WO | 2010/112618 | 10/2010 |
| WO | 2014/042752 | 3/2014 |

OTHER PUBLICATIONS

"Declaration of Dr. Morten Olgaard Jensen," IPR2018-01549, Exhibit 1002, dated Aug. 15, 2018, 103 pages.

"Declaration of Kristina Rouw, Ph.D," IPR2018-01549, Exhibit 2001, dated Nov. 29, 2018, 45 pages.

"Declaration of Kristina Rouw, Ph.D," IPR2018-01658, Exhibit 2001, dated Dec. 10, 2018, 44 pages.

"Patent Owner's Preliminary Response," IPR2018-01549, Paper 8, dated Nov. 29, 2018.

"Patent Owner's Preliminary Response," IPR2018-01658, Paper 6, dated Dec. 11, 2018.

"Petition For Inter Partes Review of U.S Pat. No. 9,089,362 Under 35 U.S.C. § 312 and 37 C.F.R. § 42.104," Cardiovascular Systems, Inc. v. Cardio Flow, Inc., IPR2018-01658, Paper 1, dated Sep. 5, 2018.

"Petition For Inter Partes Review of U.S. Pat. No. 9,788,853 Under 35 U.S.C. § 312 and 37 C.F.R. § 42.104," Cardiovascular Systems, Inc. Petitioner v. Cardio Flow, Inc. Patent Owner, IPR2018-01549, Paper 1, dated Aug. 17, 2018.

"Petition For Inter Partes Review of U.S Pat. No.9,089,362 Under 35 U.S.C. § 312 and 37 C.F.R. § 42.104," Cardiovascular Systems, Inc. Petitioner v. Cardio Flow, Inc. Patent Owner, IPR2018-01658, Paper 1, dated Sep. 5, 2018.

Declaration of Aleksey Filippov, Apr. 23, 2007, 1 page.

Declaration of Dmitri Prudnikov, Apr. 23, 2007, 1 page.

European Search Report in Application No. 15737946.2, dated Aug. 1, 2017, 8 pages.

Excerpt from Deposition of Dmitri Prudnikov, Mar. 5, 2008, 7 pages.

Excerpt from Deposition of Dmitri Prudnikov, Mar. 6, 2008, 54 pages.

Exhibits Nos. 14, 31 & 32, from Deposition of Dmitri Prudnikov, Mar. 5, 2008, 3 pages.

Exhibits Nos. 33-39 from Deposition of Dmitri Prudnikov, Mar. 6, 2008, 47 pages.

Extended European Search Report in European Appln No. 19847249.0, dated Aug. 6, 2021, 7 pages.

Invitation To Pay Additional Fees And, Where Applicable, Protest Fee in Application No. PCT/US17/26179, mailed on Jul. 6, 2017, 2 pages.

PCT Inernational Preliminary Report on Patentability in International Appln. No. PCT/EP2010/054548, dated Oct. 4, 2011, 8 pages.

PCT Inernational Preliminary Report on Patentability in International Appln. No. PCT/EP2010/054550, dated Oct. 4, 2011, 7 pages.

PCT International Preliminary Report on Patentability, in International Application No. PCT/US2015/011212, dated Jul. 19, 2016, 8 pages.

PCT International Search Report and Written Opinion in Appln. No. PCT/US2019/044893, dated Nov. 21, 2019, 16 pages.

PCT International Search Report and Written Opinion in International Application No. PCT/US2015/011212, dated May 6, 2015.

PCT International Search Report and Written Opinion in International Application No. PCT/US2017/26179, dated Oct. 4, 2017, 15 pages.

PCT International Search Report and Written Opinion in International Application No. PCT/US2018/019238, dated May 8, 2018, 16 pages.

(56) References Cited

OTHER PUBLICATIONS

PCT International Search Report corresponding to International Application No. PCT/EP2007/056516, dated Oct. 17, 2007, 3 pages.
PCT International Search Report in International Application No. PCT/EP2007/062777, dated Apr. 9, 2008, 2 pages.
PCT International Search Report in International Appln. No. PCT/EP2007/056499, dated Nov. 5, 2007, 3 pages.
PCT International Search Report in International Appln. No. PCT/EP2007/056500, dated Dec. 11, 2007, 6 pages.
PCT International Search Report, in International Appln. No. PCT/EP2008/065986, dated Feb. 26, 2009, 3 pages.

\* cited by examiner

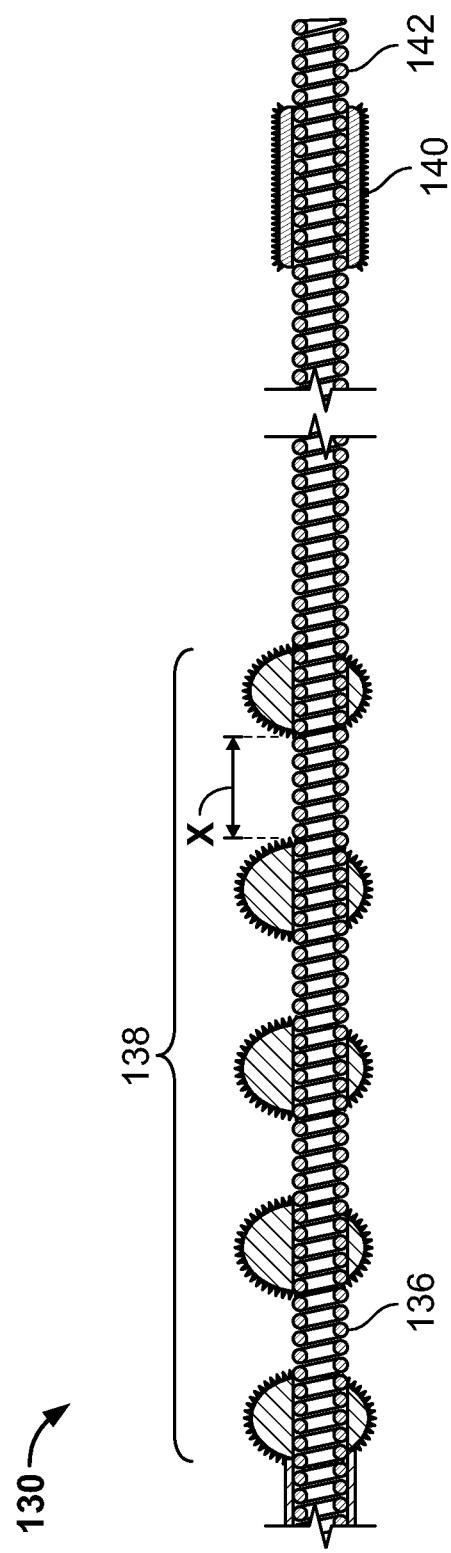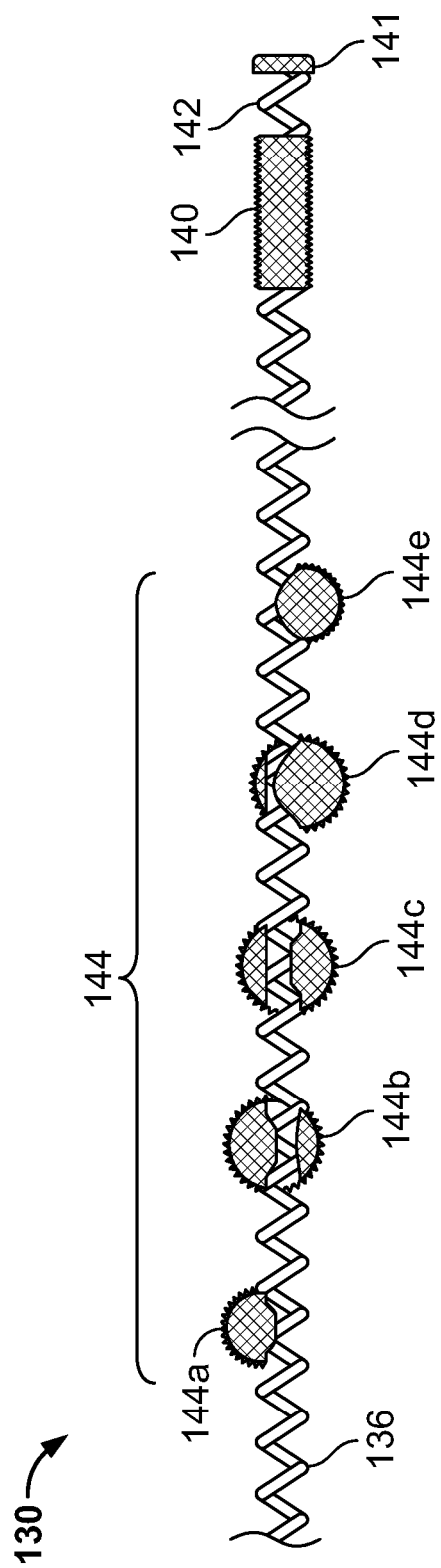

ATHERECTOMY DEVICES AND METHODS

CLAIM OF PRIORITY

This is a continuation of U.S. Application Serial No. 17/592,797 filed on Feb. 4, 2022, which is a continuation of U.S. Application Serial No. 16/530,284 filed on Aug. 2, 2019 (now U.S. Pat. No. 11,272,954), which claims the benefit of U.S. Provisional Pat. Application Serial No. 62/715,643 filed on Aug. 7, 2018, the entire contents of which are hereby incorporated by reference.

TECHNICAL FIELD

This document relates to rotational atherectomy devices and systems with an electric motor that removes or reduces stenotic lesions in blood vessels, for example, by rotating an abrasive element within the vessel to partially or completely remove the stenotic lesion material.

BACKGROUND

Atherosclerosis, the clogging of arteries with plaque, is often a result of coronary heart disease or vascular problems in other regions of the body. Plaque is made up of fat, cholesterol, calcium, and other substances found in the blood. Over time, the plaque hardens and narrows the arteries. This limits the flow of oxygen-rich blood to organs and other parts of the body.

Blood flow through the peripheral arteries (e.g., carotid, iliac, femoral, renal etc.), can be similarly affected by the development of atherosclerotic blockages. Peripheral artery disease (PAD) can be serious because without adequate blood flow, the kidneys, legs, arms, and feet may suffer irreversible damage. Left untreated, the tissue can die or harbor infection.

One method of removing or reducing such blockages in blood vessels is known as rotational atherectomy. In some implementations, a drive shaft carrying an abrasive burr or other abrasive surface (e.g., formed from diamond grit or diamond particles) rotates at a high speed within the vessel, and the clinician operator slowly advances the atherectomy device distally so that the abrasive burr scrapes against the occluding lesion and disintegrates it, reducing the occlusion and improving the blood flow through the vessel.

SUMMARY

Some embodiments of a rotational atherectomy device for removing stenotic lesion material from a blood vessel of a patient, includes: an elongate flexible drive shaft; an abrasive element coupled to a distal portion of the elongate flexible drive shaft; and a handle comprising an outer housing. The handle further includes an electric motor coupled to a proximal portion of the elongate flexible drive shaft, where the electric motor can be configured to cause rotation of the elongate flexible drive shaft in a first rotational direction. The device also includes a pump configured to provide fluid to a distal portion of the elongate flexible drive shaft, wherein the outer housing contains the electric motor and the pump.

In some embodiments, the rotational atherectomy device further comprises a control system configured to control rotation of the electric motor by monitoring an amount of current supplied to the electric motor and limiting the amount of current supplied such that the amount of current does not exceed a threshold current value. In some embodiments, the control system is configured to control rotation of the electric motor by initiating a stopping protocol when the amount of the current supplied reaches a threshold current value. In some embodiments, the stopping protocol comprises reducing the amount of current supplied to the electric motor to approximately zero. In some embodiments, the stopping protocol comprises reversing rotation of the elongate drive shaft by reversing the rotation caused by the electrical motor from the first rotational direction to a second rotational direction. In some embodiments, the stopping protocol occurs after a predetermined amount of time. In some embodiments, the predetermined amount of time is about 0.1 second to about 60 seconds. In some embodiments, the predetermined amount of time begins after the threshold current value is reached. In some embodiments, the elongate flexible drive shaft defines a longitudinal axis and comprising a torque-transmitting coil of one or more filars that are helically wound around the longitudinal axis in a second rotational direction, such that rotation of the elongate flexible drive shaft in the first rotational direction causes unwinding of the one or more filars of the elongate flexible drive shaft.

In some embodiments, the device further comprises a power source configured to couple to the handle. In some embodiments, the device further comprises a rechargeable battery removably coupled to the handle. In some embodiments, the handle further comprises a battery. In some embodiments, the handle further comprises a pump motor coupled to the pump and configured to run the pump. In some embodiments, the pump comprises at least one of a micropump, a piezoelectric pump, an electromechanical integrated pump, a peristaltic pump, or a quasiperistaltic pump. In some embodiments, the electric motor comprises at least one of a DC motor, or a DC motor controller. In some embodiments, the elongate flexible drive shaft is directly coupled to the electric motor. In some embodiments, the elongate flexible drive shaft is directly coupled to the electric motor via a cannulation in the electric motor. In some embodiments, the electric motor is coupled to the elongate flexible drive shaft in a gearless configuration. In some embodiments, the elongate flexible drive shaft is coupled to the electric motor via one or more gears. In some embodiments, the gear ratio is 2:1.

In some embodiments, a rotational atherectomy device for removing stenotic lesion material from a blood vessel of a patient, includes: an elongate flexible drive shaft defining a longitudinal axis and comprising a torque-transmitting coil; an abrasive element coupled to a distal portion of the elongate flexible drive shaft; and a handle. The handle comprises: an electric motor coupled to a proximal portion of the elongate flexible drive shaft, the electric motor configured to cause rotation of the elongate flexible drive shaft in a first rotational direction, such that rotation of the elongate flexible drive shaft in the first rotational direction causes unwinding of the elongate flexible drive shaft; and a control system configured to control rotation of the electric motor by monitoring an amount of current supplied to the electric motor; and limiting the amount of current supplied such that the amount of the current does not exceed a threshold current value.

In some embodiments, the torque-transmitting coil includes one or more filars that are helically wound around the longitudinal axis in a second rotational direction. In some embodiments, the control system is configured to control rotation of the electric motor by initiating a stopping protocol when the amount of the current supplied reaches a threshold current value. In some embodiments, the stopping protocol comprises reducing the amount of current supplied to the electric motor to approximately zero. In some embodiments, the stopping protocol comprises reversing rotation of the elongate drive shaft from the first rotational direction to the second rotational direction. In some embodiments, the device further comprises a power source configured to couple to the handle. In some embodiments, the device further comprises a rechargeable battery removably coupled to the handle. In some embodiments, the handle further comprises a battery. In some embodiments, the device further comprises a pump configured to provide fluid to a distal portion of the elongate flexible drive shaft.

In some embodiments, a method for performing rotational atherectomy to remove stenotic lesion material from a blood vessel of a patient, includes: delivering a rotational atherectomy device into the blood vessel. The rotational atherectomy device comprises: an elongate flexible drive shaft; an abrasive element coupled to a distal portion of the elongate flexible drive shaft; and a handle comprising an outer housing. The handle further comprises: an electric motor coupled to a proximal portion of the elongate flexible drive shaft, the electric motor configured to cause rotation of the elongate flexible drive shaft in a first rotational direction; and a pump configured to provide fluid to a distal portion of the elongate flexible drive shaft, wherein the outer housing contains the electric motor and the pump. The method further includes rotating the drive shaft about the longitudinal axis in the first rotational direction.

In some embodiments, a method for performing rotational atherectomy to remove stenotic lesion material from a blood vessel of a patient, includes: delivering a rotational atherectomy device into the blood vessel, and rotating the drive shaft about the longitudinal axis in the first rotational direction. The rotational atherectomy device comprises: an elongate flexible drive shaft defining a longitudinal axis and comprising a torque-transmitting coil; an abrasive element coupled to a distal portion of the elongate flexible drive shaft; and a handle, comprising: an electric motor coupled to a proximal portion of the elongate flexible drive shaft, the electric motor configured to cause rotation of the elongate flexible drive shaft in a first rotational direction, such that rotation of the elongate flexible drive shaft in the first rotational direction causes unwinding of the elongate flexible drive shaft; and a control system configured to control rotation of the electric motor.

In some embodiments, the torque-transmitting coil comprising one or more filars that are helically wound around the longitudinal axis in a second rotational direction. In some embodiments, the method further comprises: monitoring an amount of current supplied to the electric motor; and limiting the amount of current supplied such that the amount of the current does not exceed a threshold current value. In some embodiments, the method further comprises initiating a stopping protocol when the amount of the current supplied reaches a threshold current value. In some embodiments, the stopping protocol comprises at least one of reducing the amount of current supplied to the electric motor to approximately zero or reversing rotation of the elongate drive shaft from the first rotational direction to a second rotational direction.

In some embodiments, a rotational atherectomy device for removing stenotic lesion material from a blood vessel of a patient, includes: an elongate flexible drive shaft defining a longitudinal axis and comprising a torque-transmitting coil; an abrasive element coupled to a distal portion of the elongate flexible drive shaft; and a handle. The handle comprises: an electric motor coupled to a proximal portion of the elongate flexible drive shaft, the electric motor configured to cause rotation of the elongate flexible drive shaft in a first rotational direction, such that rotation of the elongate flexible drive shaft in the first rotational direction causes unwinding of the elongate flexible drive shaft; and a control system configured to control rotation of the electric motor by exclusively monitoring an amount of current supplied to the electric motor and limiting the amount of current supplied such that the amount of the current does not exceed a threshold current value.

In some embodiments, the threshold current value is configured to limit rotation of the elongate flexible drive shaft in the first rotational direction such that there is no unwinding of the one or more filars of the elongate flexible drive shaft. In some embodiments, the threshold current value is configured to limit rotation of the elongate flexible drive shaft in the first rotational direction such that there is no change in a maximum diameter of the elongate flexible drive shaft.

In some embodiments, a rotational atherectomy device for removing stenotic lesion material from a blood vessel of a patient, includes: an elongate flexible drive shaft; an abrasive element coupled to a distal portion of the elongate flexible drive shaft; and a handle comprising an outer housing. The handle further comprises: an electric motor comprising a cannula configured to receive the elongate flexible drive shaft, wherein the electric motor is coupled to a proximal portion of the elongate flexible drive shaft and configured to rotate the elongate flexible drive shaft in a first rotational direction.

Some of the embodiments described herein may provide one or more of the following advantages. First, some embodiments of the rotational atherectomy system are configured to advance the drive shaft and the handle assembly over a guidewire, and to use an electric motor to drive the rotation of the drive shaft while the guidewire remains within the drive shaft. Accordingly, in some embodiments the handle assemblies provided herein include features that allow the drive shaft to be positioned over a guidewire. Thereafter, the guidewire can be detained in relation to the handle so that the guidewire will not rotate while the drive shaft is being rotated.

Second, some embodiments of the rotational atherectomy system include a drive shaft constructed of one or more helically wound filars that are wound in the same direction that the drive shaft is rotated during use. Accordingly, the turns of the helically wound filars can tend to radially expand and separate from each other (or "open up") during rotational use. Such a scenario advantageously reduces frictional losses between adjacent filar turns. Additionally, when a guidewire is disposed within the lumen defined by the helically wound filars during rotational use, the drive shaft will tend to loosen on the guidewire rather than to tighten on it. Consequently, in some cases no use of lubricant between the guidewire and the drive shaft is necessary. Moreover, since the drive shaft will tend to loosen on the guidewire, less stress will be induced on the guidewire during rotation of the drive shaft. Thus, the potential for causing breaks of the guidewire is advantageously reduced. Further, since the drive shaft will tend to loosen on the guidewire during use, a larger guidewire can be advantageously used in some cases.

Third, some embodiments of the rotational atherectomy devices and systems provided herein include multiple abrasive elements that are offset from each other around the drive shaft such that the centers of mass of the abrasive elements define a path that spirals around a central longitudinal axis of the drive shaft. In particular embodiments, the rotational atherectomy systems are used by rotating the drive shaft around the longitudinal axis in a direction opposite of the spiral path defined by the centers of mass of the abrasive elements. Such an arrangement can advantageously provide a smoother running and more controllable atherectomy procedure as compared to systems that rotate the drive shaft in the same direction as the spiral path defined by the centers of mass of the abrasive elements.

Fourth, some embodiments of the rotational atherectomy devices and systems provided herein include a handle assembly with an electric motor that is used to drive rotations of the drive shaft. Such an electric motor can be entirely or substantially entirely housed within the handle assembly of the rotational atherectomy devices. The electric motor can provide the benefits of providing increased control and reliability over the rotational movement of the shaft. Such benefits can improve the rotational responsiveness of rotational actuation of the shaft and can reduce or eliminate unintentional or excessive rotational actuation during an atherectomy procedure. Furthermore, the electric motor does not rely on pneumatic equipment, and therefore eliminates the burden of providing pneumatic power, such as a compressed gas (e.g., air, nitrogen, or the like) supply, during a medical procedure. Additionally, the handle assembly can incorporate or externally couple a control system for monitoring and controlling the rotation of the electric motor.

Fifth, certain embodiments of the handle assembly may integrate a pump or micropump, such as a saline pump (with a pump motor), within the housing. The pump can provide the benefit of delivering saline, or other fluids, to a distal end of the rotational atherectomy device, providing lubrication, and/or preventing blood from back flowing through a sheath of the rotational atherectomy device outside of the body. The integrated pump can increase the versatility of the handle assembly by eliminating the need to obtain and connect an external pump to the handle assembly during a medical procedure.

Also, by integrating the electric motor and pump into the handle assembly, additional advantages can be realized. For example, the handle assembly and/or the entire rotational atherectomy system provided herein can be sterilizable as well as disposable, thus reducing the risk of contamination and infection.

Sixth, the handle assembly can also house a battery, or couple to a battery. Such a device would not need external power to operate, making the rotational atherectomy device more readily available in remote areas with limited power supplies, or provide the user with increased convenience of use. As such, a clinician can have increased mobility with the handle assembly, as the handle assembly only needs to attach to an external fluid reservoir. Accordingly, a clinician would be less restricted and obstructed by connection cables during use.

Seventh, in some embodiments rotational atherectomy systems described herein include user controls that are convenient and easy to operate. In one such example, the user controls can include selectable elements on the handle assembly, reducing the need for a clinician to operate a secondary control device while operating the handle assembly. For example, the user controls can include selectable elements that correspond to the speed of drive shaft rotations. In some such examples, the user can conveniently select "low" or "high" speeds. Hence, in such a case the clinician-user conveniently does not need to explicitly select or control the rpm of the drive shaft.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 is a longitudinal cross-sectional view of a distal portion of an example rotational atherectomy device showing a multi-portion abrasive element and a distal stability element with an abrasive coating, in accordance with some embodiments.

FIG. 11 is a side view of a distal portion of another example rotational atherectomy device showing a multi-portion abrasive element and a distal stability element with an abrasive coating, with an unwinding of the drive shaft (note that the figure shows unwinding in an exaggerated form for instructive purposes), in accordance with some embodiments.

Like reference symbols in the various drawings indicate like elements.

DETAILED DESCRIPTION OF ILLUSTRATIVE EMBODIMENTS

Figure 1:
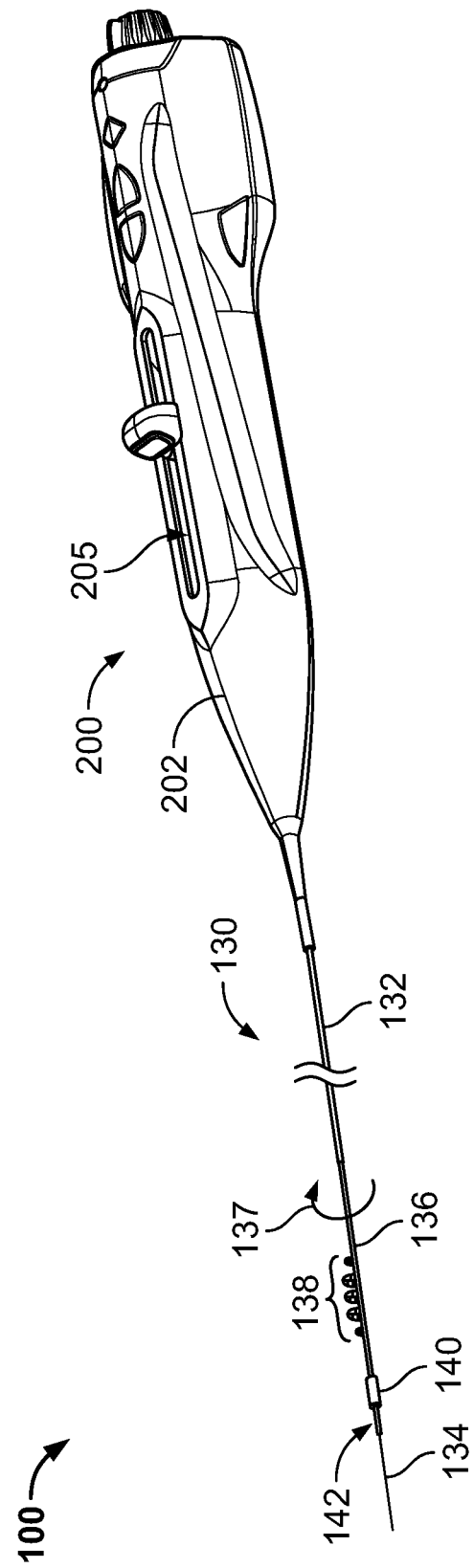
FIG. 1 is a perspective view of an example rotational atherectomy system in accordance with some embodiments.

Referring to FIG. 1, in some embodiments a rotational atherectomy system 100 for removing or reducing stenotic lesions in blood vessels can include a guidewire 134, a handle assembly 200, and an elongate flexible drive shaft assembly 130. The drive shaft assembly 130 extends distally from the handle assembly 200. The handle assembly 200 can be operated by a clinician to perform and control the rotational atherectomy procedure.

In the depicted embodiment, the elongate flexible drive shaft assembly 130 includes a sheath 132 and a flexible drive shaft 136. A proximal end of the sheath 132 is fixed to a distal end of the handle assembly 200. The flexible drive shaft 136 is slidably and rotatably disposed within a lumen of the sheath 132. The flexible drive shaft 136 defines a longitudinal lumen in which the guidewire 134 is slidably disposed. In this embodiment, the flexible drive shaft 136 includes a torque-transmitting coil that defines the longitudinal lumen along a central longitudinal axis, and the drive 136 shaft is configured to rotate about the longitudinal axis while the sheath 132 remains generally stationary. Hence, as described further below, during a rotational atherectomy procedure the flexible drive shaft 136 is in motion (e.g., rotating and longitudinally translating) while the sheath 132 and the guidewire 134 are generally stationary.

In some optional embodiments, an inflatable member (not shown) can surround a distal end portion of the sheath 132. Such an inflatable member can be selectively expandable between a deflated low-profile configuration and an inflated deployed configuration. The sheath 132 may define an inflation lumen through which the inflation fluid can pass (to and from the optional inflatable member). The inflatable member can be in the deflated low-profile configuration during the navigation of the drive shaft assembly 130 through the patient's vasculature to a target location in a vessel. Then, at the target location, the inflatable member can be inflated so that the outer diameter of the inflatable member contacts the wall of the vessel. In that arrangement, the inflatable member advantageously stabilizes the drive shaft assembly 130 in the vessel during the rotational atherectomy procedure.

Still referring to FIG. 1, the flexible driveshaft 136 is slidably and rotatably disposed within a lumen of the sheath 132. A distal end portion of the driveshaft 136 extends distally of the distal end of the sheath 132 such that the distal end portion of the driveshaft 136 is exposed (e.g., not within the sheath 132, at least not during the performance of the actual rotational atherectomy).

In the depicted embodiment, the exposed distal end portion of the driveshaft 136 includes one or more abrasive elements 138, a (optional) distal stability element 140, and a distal drive shaft extension portion 142. In the depicted embodiment, the one or more abrasive elements 138 are eccentrically-fixed to the driveshaft 136 proximal of the distal stability element 140. In this embodiment, the distal stability element 140 is concentrically-fixed to the driveshaft 136 between the one or more abrasive elements 138 and the distal drive shaft extension portion 142. As such, the center of mass of the distal stability element 140 is aligned with the central axis of the drive shaft 136 while the center of mass of each abrasive element 138 is offset from the central axis of the drive shaft 136. The distal drive shaft extension portion 142, which includes the torque-transmitting coil, is configured to rotate about the longitudinal axis extends distally from the distal stability element 140 and terminates at a free end of the drive shaft 136.

In some optional embodiments, a proximal stability element (not shown) is included. The proximal stability element can be constructed and configured similarly to the depicted embodiment of the distal stability element 140 (e.g., a metallic cylinder directly coupled to the torque-transmitting coil of the drive shaft 136 and concentric with the longitudinal axis of the drive shaft 136) while being located proximal to the one or more abrasive elements 138.

In the depicted embodiment, the distal stability element 140 has a center of mass that is axially aligned with a central longitudinal axis of the drive shaft 136, while the one or more abrasive elements 138 (collectively and/or individually) have a center of mass that is axially offset from central longitudinal axis of the drive shaft 136. Accordingly, as the drive shaft 136 is rotated about its longitudinal axis, the principle of centrifugal force will cause the one or more abrasive elements 138 (and the portion of the drive shaft 136 to which the one or more abrasive elements 138 are affixed) to follow a transverse generally circular orbit (e.g., somewhat similar to a "jump rope" orbital movement) relative to the central axis of the drive shaft 136. In general, faster speeds (rpm) of rotation of the drive shaft 136 will result in larger diameters of the orbit (within the limits of the vessel diameter). The orbiting one or more abrasive elements 138 will contact the stenotic lesion to ablate or abrade the lesion to a reduced size (i.e., small particles of the lesion will be abraded from the lesion).

The rotating distal stability element 140 will remain generally at the longitudinal axis of the drive shaft 136 as the drive shaft 136 is rotated. In some optional embodiments, two or more distal stability elements 140 are included. As described further below, contemporaneous with the rotation of the drive shaft 136, the drive shaft 136 can be translated back and forth along the longitudinal axis of the drive shaft 136. Hence, lesions can be abraded radially and longitudinally by virtue of the orbital rotation and translation of the one or more abrasive elements 138, respectively.

The flexible drive shaft 136 of rotational atherectomy system 100 is laterally flexible so that the drive shaft 136 can readily conform to the non-linear vasculature of the patient, and so that a portion of the drive shaft 136 at and adjacent to the one or more abrasive elements 138 will laterally deflect when acted on by the centrifugal forces resulting from the rotation of the one or more eccentric abrasive elements 138. In this embodiment, the drive shaft 136 comprises one or more helically wound wires (or filars) that provide one or more torque-transmitting coils of the drive shaft 136 (as described below, for example, in connection with FIGS. 8-11). In some embodiments, the one or more helically wound wires are made of a metallic material such as, but not limited to, stainless steel (e.g., 316, 316L, or 316LVM), nitinol, titanium, titanium alloys (e.g., titanium beta 3), carbon steel, or another suitable metal or metal alloy. In some alternative embodiments, the filars are or include graphite, Kevlar, or a polymeric material. In some embodiments, the filars can be woven, rather than wound. In some embodiments, individual filars can comprise multiple strands of material that are twisted, woven, or otherwise coupled together to form a filar. In some embodiments, the filars have different cross-sectional geometries (size or shape) at different portions along the axial length of the drive shaft 136. In some embodiments, the filars have a cross-sectional geometry other than a circle, e.g., an ovular, square, triangular, or another suitable shape.

In this embodiment, the drive shaft 136 has a hollow core. That is, the drive shaft 136 defines a central longitudinal lumen running therethrough. The lumen can be used to slidably receive the guidewire 134 therein, as will be described further below. In some embodiments, the lumen can be used to aspirate particulate or to convey fluids that are beneficial for the atherectomy procedure.

In some embodiments, the drive shaft 136 includes an optional coating on one or more portions of the outer diameter of the drive shaft 136. The coating may also be described as a jacket, a sleeve, a covering, a casing, and the like. In some embodiments, the coating adds column strength to the drive shaft 136 to facilitate a greater ability to push the drive shaft 136 through stenotic lesions. In addition, the coating can enhance the rotational stability of the drive shaft 136 during use. In some embodiments, the coating is a flexible polymer coating that surrounds an outer diameter of the coil (but not the abrasive elements 138 or the distal stability element 140) along at least a portion of drive shaft 136 (e.g., the distal portion of the drive shaft 136 exposed outwardly from the sheath 132). In some embodiments, a portion of the drive shaft 136 or all of the drive shaft 136 is uncoated. In particular embodiments, the coating is a fluid impermeable material such that the lumen of the drive shaft 136 provides a fluid impermeable flow path along at least the coated portions of the drive shaft 136.

The coating may be made of materials including, but not limited to, PEBEX, PICOFLEX, PTFE, ePTFE, FEP, PEEK, silicone, PVC, urethane, polyethylene, polypropylene, and the like, and combinations thereof. In some embodiments, the coating covers the distal stability element 140 and the distal extension portion 142, thereby leaving only the one or more abrasive elements 138 exposed (non-coated) along the distal portion of the drive shaft 136. In alternative embodiments, the distal stability element 140 is not covered with the coating, and thus would be exposed like the abrasive element 140. In some embodiments, two or more layers of the coating can be included on portions of the drive shaft 136. Further, in some embodiments different coating materials (e.g., with different durometers and/or stiffnesses) can be used at different locations on the drive shaft 136.

In the depicted embodiment, the distal stability element 140 is a metallic cylindrical member having an inner diameter that surrounds a portion of the outer diameter of the drive shaft 136. In some embodiments, the distal stability element 140 has a longitudinal length that is greater than a maximum exterior diameter of the distal stability element 140. In the depicted embodiment, the distal stability element 140 is coaxial with the longitudinal axis of the drive shaft 136. Therefore, the center of mass of the distal stability element 140 is axially aligned (non-eccentric) with the longitudinal axis of the drive shaft 136. In alternative rotational atherectomy device embodiments, stability element(s) that have centers of mass that are eccentric in relation to the longitudinal axis may be included in addition to, or as an alternative to, the coaxial stability elements 140. For example, in some alternative embodiments, the stability element(s) can have centers of mass that are eccentric in relation to the longitudinal axis and that are offset 180 degrees (or otherwise oriented) in relation to the center of mass of the one or more abrasive elements 138.

The distal stability element 140 may be made of a suitable biocompatible material, such as a higher-density biocompatible material. For example, in some embodiments the distal stability element 140 may be made of metallic materials such as stainless steel, tungsten, molybdenum, iridium, cobalt, cadmium, and the like, and alloys thereof. The distal stability element 140 has a fixed outer diameter. That is, the distal stability element 140 is not an expandable member in the depicted embodiment. The distal stability element 140 may be mounted to the filars of the drive shaft 136 using a biocompatible adhesive, by welding, by press fitting, and the like, and by combinations thereof. The coating may also be used in some embodiments to attach or to supplement the attachment of the distal stability element 140 to the filars of the drive shaft 136. Alternatively, the distal stability element 140 can be integrally formed as a unitary structure with the filars of the drive shaft 136 (e.g., using filars of a different size or density, using filars that are double-wound to provide multiple filar layers, or the like). The maximum outer diameter of the distal stability element 140 may be smaller than the maximum outer diameters of the one or more abrasive elements 138.

In some embodiments, the distal stability element 140 has an abrasive coating on its exterior surface. For example, in some embodiments a diamond coating (or other suitable type of abrasive coating) is disposed on the outer surface of the distal stability element 140. In some cases, such an abrasive surface on the distal stability element 140 can help facilitate the passage of the distal stability element 140 through vessel restrictions (such as calcified areas of a blood vessel).

In some embodiments, the distal stability element 140 has an exterior cylindrical surface that is smoother and different from an abrasive exterior surface of the one or more abrasive elements 138. That may be the case whether or not the distal stability element 140 have an abrasive coating on its exterior surface. In some embodiments, the abrasive coating on the exterior surface of the distal stability element 140 is rougher than the abrasive surfaces on the one or more abrasive elements 138.

Still referring to FIG. 1, the one or more abrasive elements 138 (which may also be referred to as a burr, multiple burrs, or (optionally) a helical array of burrs) can comprise a biocompatible material that is coated with an abrasive media such as diamond grit, diamond particles, silicon carbide, and the like. In the depicted embodiment, the abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating, such as a diamond grit coating.

In the depicted embodiment, the two outermost abrasive elements are smaller in maximum diameter than the three inner abrasive elements. In some embodiments, all of the abrasive elements are the same size. In particular embodiments, three or more different sizes of abrasive elements are included. Any and all such possible arrangements of sizes of abrasive elements are envisioned and within the scope of this disclosure.

Also, in the depicted embodiment, the center of mass of each abrasive element 138 is offset from the longitudinal axis of the drive shaft 136. Therefore, as the eccentric one or more abrasive elements 138 are rotated (along an orbital path), at least a portion of the abrasive surface of the one or more abrasive elements 138 can make contact with surrounding stenotic lesion material. As with the distal stability element 140, the eccentric one or more abrasive elements 138 may be mounted to the filars of the torque-transmitting coil of the drive shaft 136 using a biocompatible adhesive, high temperature solder, welding, press fitting, and the like. In some embodiments, a hypotube is crimped onto the driveshaft and an abrasive element is laser welded to the hypotube. Alternatively, the one or more abrasive elements 138 can be integrally formed as a unitary structure with the filars of the drive shaft 136 (e.g., using filars that are wound in a different pattern to create an axially offset structure, or the like).

In some embodiments, the spacing of the distal stability element 140 relative to the one or more abrasive elements 138 and the length of the distal extension portion 142 can be selected to advantageously provide a stable and predictable rotary motion profile during high-speed rotation of the drive shaft 136. For example, in embodiments that include the distal driveshaft extension portion 142, the ratio of the length of the distal driveshaft extension 142 to the distance between the centers of the one or more abrasive elements 138 and the distal stability element 140 is about 1:0.5, about 1:0.8, about 1:1, about 1.1:1, about 1.2:1, about 1.5:1, about 2:1, about 2.5:1, about 3:1, or higher than 3:1.

Figure 2:
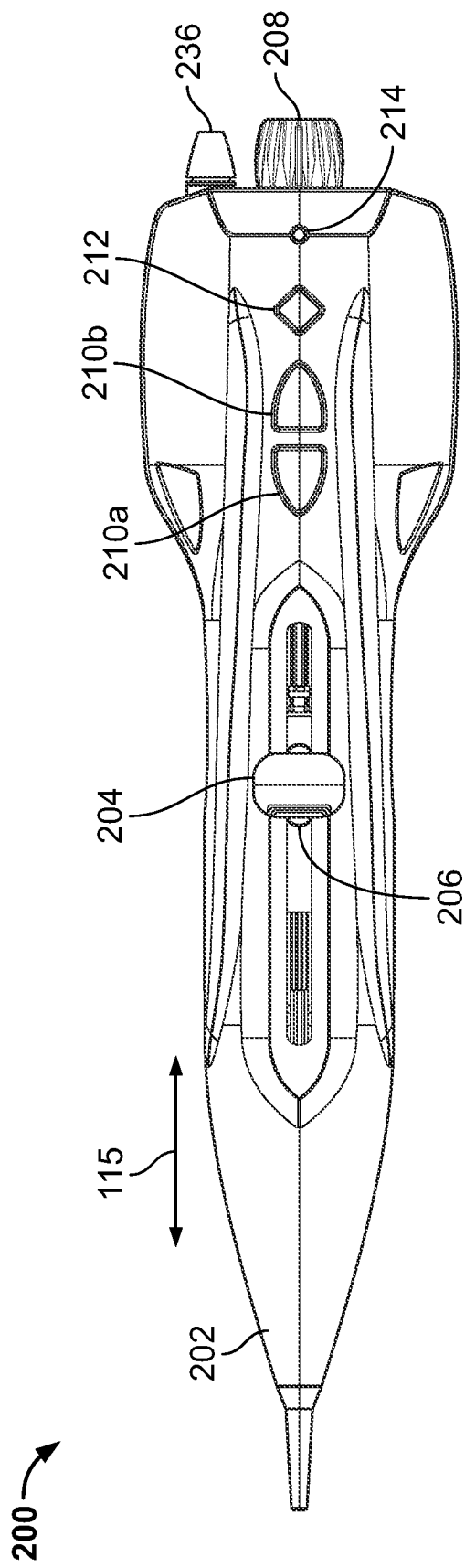
FIG. 2 is a top view of a handle assembly of the rotational atherectomy system of FIG. 1 in accordance with some embodiments.
Figure 3:
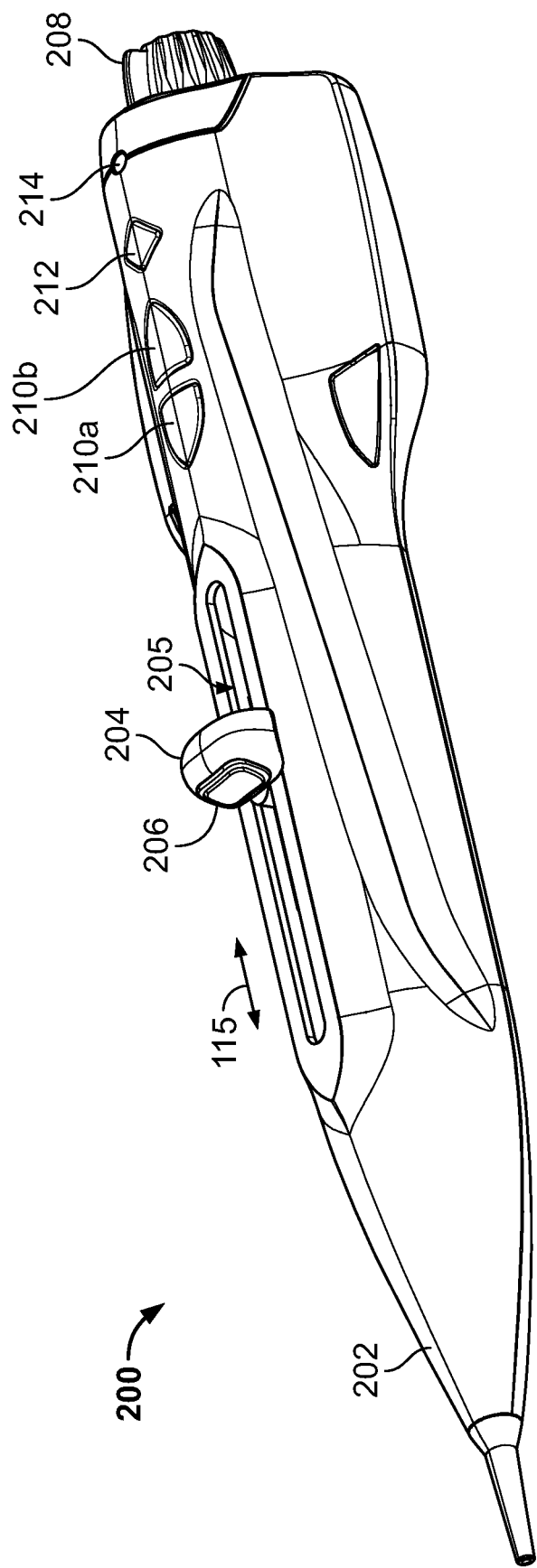
FIG. 3 is a perspective view of the handle assembly of FIG. 2 in accordance with some embodiments.
Figure 4:
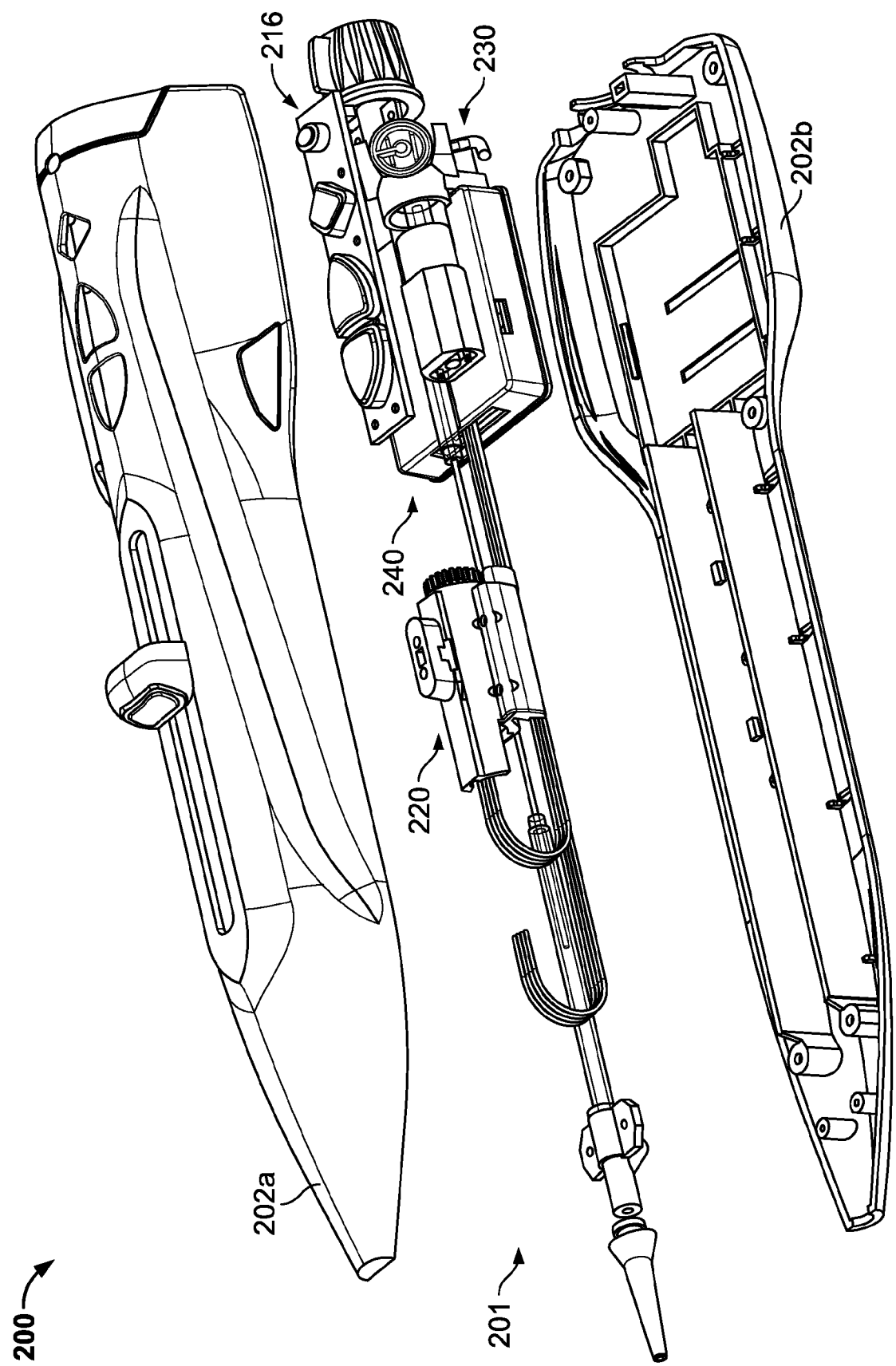
FIG. 4 is an exploded view of the handle assembly of FIG. 2 in accordance with some embodiments.

Still referring to FIG. 1, and further referring to FIGS. 2 and 3, the rotational atherectomy system 100 also includes the handle assembly 200. The handle assembly 200 includes a housing 202 and a carriage assembly 204. The carriage assembly 204 is slidably translatable along the longitudinal axis of the handle assembly 200 along an aperture 205 defining a path, such that carriage assembly 204 along the longitudinal axis as indicated by the arrow 115. For example, in some embodiments the carriage assembly 204 can be translated, without limitation, about 8 cm to about 12 cm, or about 6 cm to about 10 cm, or about 4 cm to about 8 cm, or about 6 cm to about 14 cm. As the carriage assembly 204 is translated in relation to the housing 202, the drive shaft 136 translates in relation to the sheath 132 in a corresponding manner.

In the depicted embodiment, the carriage assembly 204 includes an electrical motor switch 206. While the electrical motor switch 206 is depressed, power is supplied to the electric motor (as shown in FIGS. 4-6, and 7A-7B) which is fixedly coupled to the drive shaft 136. Hence, an activation of the electrical motor switch 206 will result in a rotation of the turbine member and, in turn, the drive shaft 136 (as depicted by arrow 137). It should be understood that the rotational atherectomy system 100 is configured to rotate the drive shaft 136 at a high speed of rotation (e.g., 20,000-160,000 rpm) such that the eccentric one or more abrasive elements 138 revolve in an orbital path to thereby contact and remove portions of a target lesion (even those portions of the lesion that are spaced farther from the axis of the drive shaft 136 than the maximum radius of the one or more abrasive elements 138).

To operate the handle assembly 200 during a rotational atherectomy procedure, a clinician can grasp the carriage assembly 204 and depress the electrical motor switch 206 with the same hand. The clinician can move (translate) the carriage assembly 204 distally and proximally by hand (e.g., back and forth in relation to the housing 202), while maintaining the electrical motor switch 206 in the depressed state. In that manner, a target lesion(s) can be ablated radially and longitudinally by virtue of the resulting orbital rotation and translation of the one or more abrasive elements 138, respectively.

To further operate the handle assembly 200 during a rotational atherectomy procedure, a clinician can select a rotational speed using electrical switches 210a and 210b. In some cases, the rotational speed can be selected through a range of speeds with electrical switch 210a causing an increase in speed and electrical switch 210b causing a decrease in speed. In some embodiments, rotational speed is changed incrementally between a plurality of preset speeds. For example, a single depression of electrical switch 210a or 210b will cause an incremental change in speed. In some embodiments, depression of the electrical switch 210a or 210b will cause a change in speed corresponding to a length of time that the electrical switch 210a or 210b is depressed. In another embodiment, the electrical switch 210a will cause a selection of a "high" rotational speed and the electrical switch 210b will cause a selection of a "low" rotational speed, in comparison to the high rotational speed.

Optionally, the electrical switches 210a and 210b can also include a light indicator. For example, when the electrical switches 210a and 210b allow for selection for a "high" and "low" speed, respectively, the electrical switches 210a and 210b can each have a single light, such that when a speed is selected, the light corresponding to the selected electrical switch 210a or 210b is illuminated to inform a clinician of the selected speed. In some embodiments, the light can shine through electrical switches 210a and 210b. Alternatively, a light can be positioned proximal electrical switch 210a and 210b. As another example, when the electrical switches 210a and 210b allow modification of a speed between a range of speeds, the light indicator can be a light bar, such that a number of lights illuminated on the light bar correspond to a selected speed.

Optionally, handle assembly 200 can include an electrical pump switch 212. Electrical pump switch 212 can turn a saline pump on and off. In some cases, a first depression of the electrical pump switch 212 will turn the saline pump on, while a second depression will turn the saline pump on. In some embodiments, the electrical pump switch 212 includes a light indicator, such that when the pump is on, a light is illuminated to inform the clinician that the pump is on.

During an atherectomy treatment, in some cases the guidewire 134 is left in position in relation to the drive shaft 136 generally as shown. For example, in some cases the portion of the guidewire 134 that is extending beyond the distal end of the drive shaft 136 (or extension portion 142) is about 10 inches to about 12 inches (about 25 cm to about 30 cm), about 6 inches to about 16 inches (about 15 cm to about 40 cm), or about 2 inches to about 20 inches (about 5 cm to about 50 cm). In some cases, the guidewire 134 is pulled back to be within (while not extending distally from) the drive shaft 136 during an atherectomy treatment. The distal end of the guidewire 134 may be positioned anywhere within the drive shaft 136 during an atherectomy treatment. In some cases, the guidewire 134 may be completely removed from within the drive shaft during an atherectomy treatment. The extent to which the guidewire 134 is engaged with the drive shaft 136 during an atherectomy treatment may affect the size of the orbital path of the one or more abrasive elements 138. Accordingly, the extent to which the guidewire 134 is engaged with the drive shaft 136 may be situationally selected to be well-suited for a particular patient anatomy, physician's preference, type of treatment being delivered, and other such factors.

In the depicted embodiment, the handle assembly 200 also includes a guidewire detention mechanism 208. The guidewire detention mechanism 208 can be selectively actuated (e.g., rotated) to releasably clamp and maintain the guidewire 134 in a stationary position relative to the handle assembly 200 (and, in turn, stationary in relation to rotations of the drive shaft 136 during an atherectomy treatment). While the drive shaft 136 and handle assembly 200 are being advanced over the guidewire 134 to put the one or more abrasive elements 138 into a targeted position within a patient's vessel, the guidewire detention mechanism 208 will be unactuated so that the handle assembly 200 is free to slide in relation to the guidewire 134. Then, when the clinician is ready to begin the atherectomy treatment, the guidewire detention mechanism 208 can be actuated to releasably detain/lock the guidewire 134 in relation to the handle assembly 200. That way the guidewire 134 will not rotate while the drive shaft 136 is rotating, and the guidewire 134 will not translate while the carriage assembly 204 is being manually translated.

In some embodiments, when the guidewire detention mechanism 208 is actuated to detain/lock the guidewire 134, a light indicator 214 can illuminate, such that a clinician can confirm the guidewire detention mechanism 208 is actuated.

Optionally, the handle assembly 200 can include a safety mechanism regarding operation of the handle assembly. For example, rotation of the drive shaft assembly 130 may be prohibited until the guidewire detention mechanism 208 is actuated, the pump has been turned on via electrical pump switch 212, and a rotation speed has been selected via electrical switch 210a or 210b. As another example, the indicator lights associated with the electrical switch 210a or 210b, the electrical pump switch 212, and the guidewire detention mechanism 208 light indicator 214 will alert a clinician that the rotational atherectomy system 100 should not be operated until all three systems (the motor, the pump, the guidewire lock) are lit. For example, each system may have a green light, such that three green lights indicates the clinician can proceed with the atherectomy procedure. Optionally, only the guidewire detection mechanism 208 needs to be actuated to allow rotation of the rotational atherectomy system 100.

Referring to FIGS. 4-6, and 7A-7B, an interior cavity 201 of the handle assembly 200 is shown. The housing 202 can include an upper housing 202a and a lower housing 202b that encapsulate a motor assembly 220, a pump assembly 230, and a controller assembly 240. The interior cavity 201 can also house the electrical switches 210a and 210b, the electrical pump switch 212, and the light indicator 214, collectively, user controls 216. In some cases, the user controls 216 can protrude through apertures of upper housing 202a. In some embodiments, the user controls 216 can abut a flexible portion of upper housing 202a, such that the user controls 216 can be actuated without direct contact. In some embodiments, the handle assembly 200 is disposable. In some embodiments, the handle assembly 200 is a sterilized handle assembly, or is partially or fully sterilizable handle assembly. For example, in some embodiments, the handle can be sterilized using ethylene oxide (EtO) sterilization, or hydrogen peroxide sterilization.

Figure 7A:
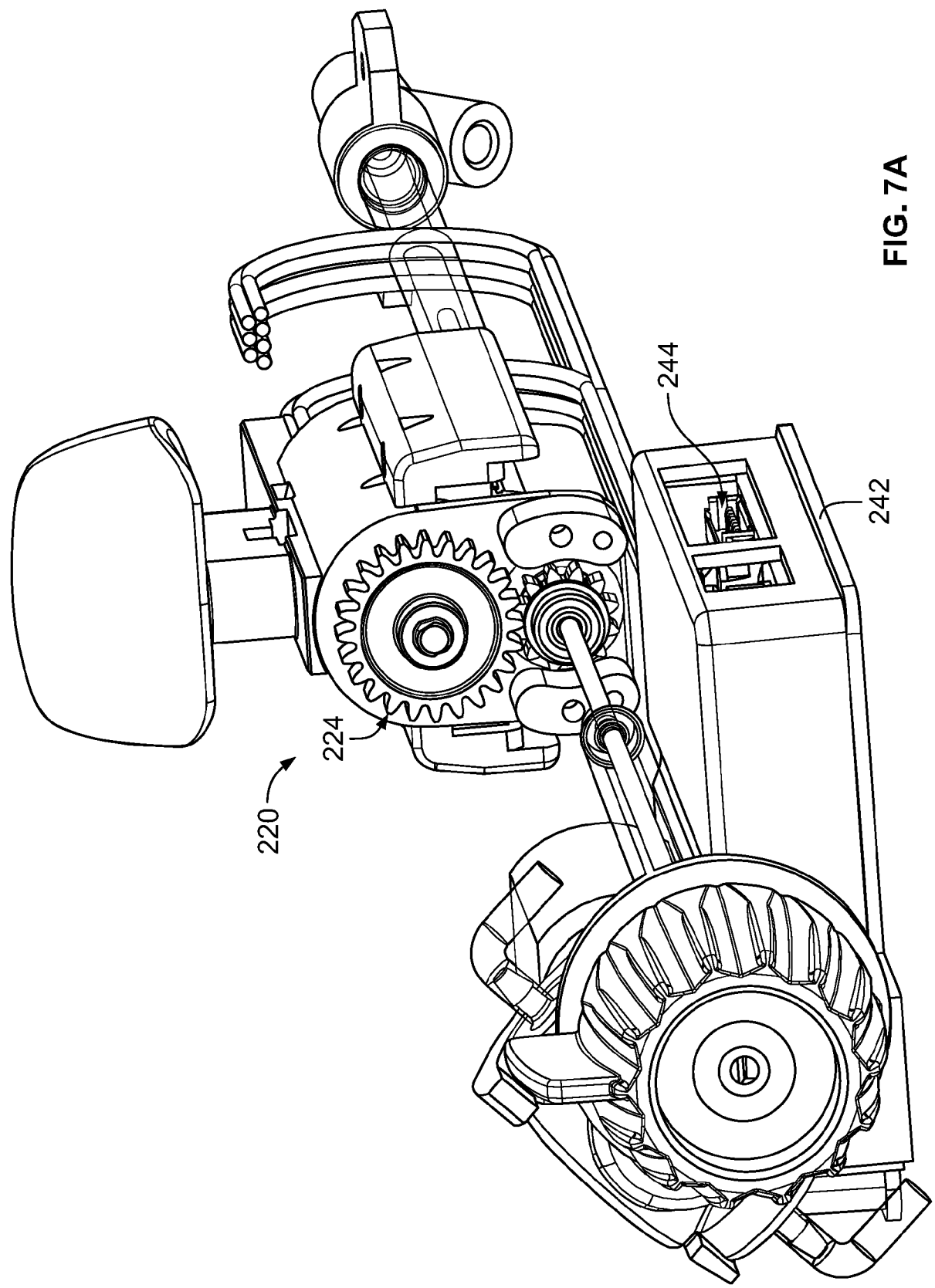

The motor assembly 220 can include a motor 222 and, optionally, a gear assembly 224 (as shown in FIG. 7A). The motor 222 can be electric motor, such as a DC motor. Exemplary motors can include a brush DC motor, or a brushless DC motor. Other suitable motors may, however, include a servo motor, a stepper motor, and/or an AC motor. Motor 222 can be mechanically coupled to carriage assembly 204, such that motor 222 can translate along housing 202, and more specifically, inside sheath 132 to cause translation of drive shaft 136. Further, motor 222 can be electrically coupled to electrical motor switch 206, such that depression of electrical motor switch 206 causes motor 222 to run. In some embodiments, motor 222 can be directly coupled to drive shaft 136 to cause rotation of drive shaft 136, and accordingly, abrasive elements 138. For example, the motor 222 can include a cannulation through a longitudinal axis of the motor 222 that is configured to receive and secure the drive shaft 136, direct drive of the drive shaft 136.

As mentioned above, motor assembly 220 can include a gear assembly 224. In some embodiments, the gear assembly 224 can have a 2:1 gear ratio to increase an rpm output from motor 222. In some cases, using a motor with lower rpm capabilities, but supplementing the motor 222 with the gear assembly 224 can be more cost effective, especially for a disposable handle assembly 200. For example, motor 222 can have an output of 40k rpm, and can cause rotation of the drive shaft 136 at 80k rpm. Motor 222 can be controlled by controller assembly 240, as will be described below.

Figure 7B:
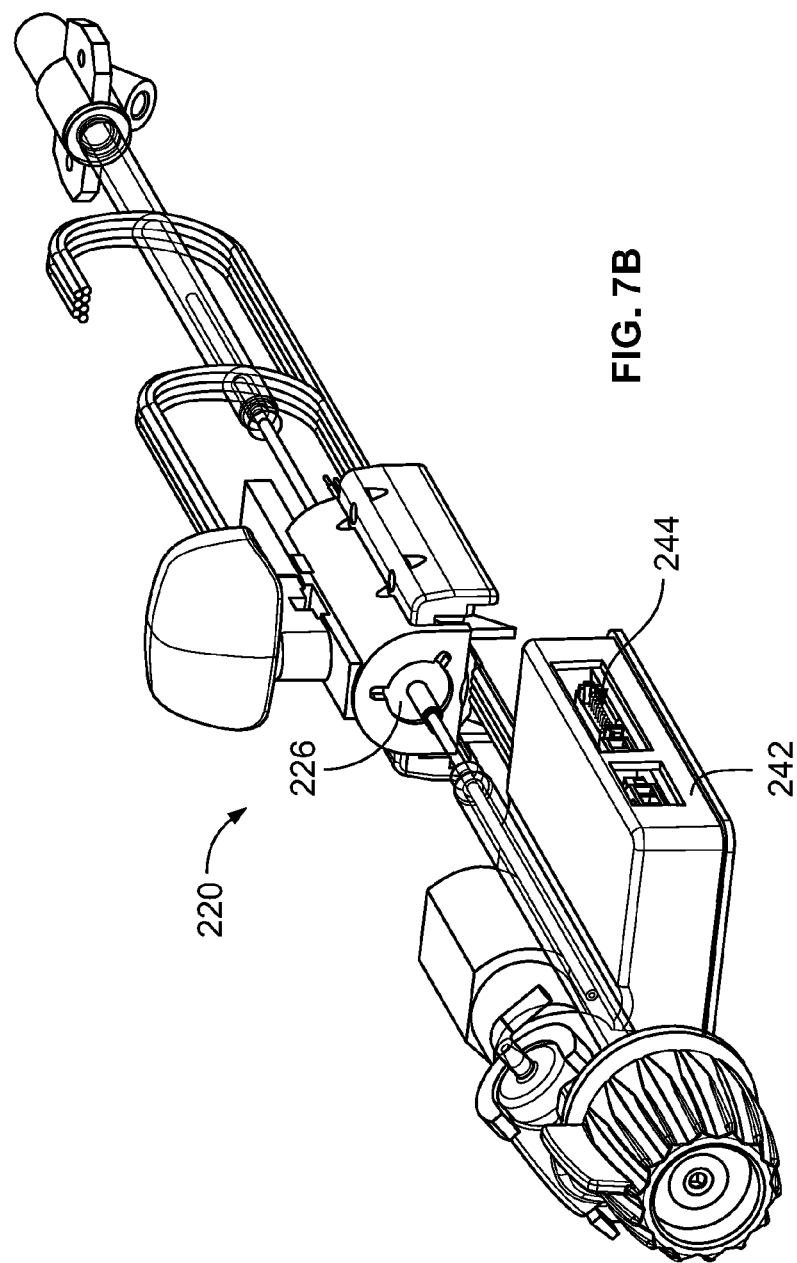

In another embodiment, as shown in FIG. 7B, motor assembly 220 can include a cannulated motor 226. Cannulated motor 226 can include a cannulation to receive a hypotube of the rotational atherectomy device. In some embodiments, the cannulated motor 226 can provide a simpler design, which can reduce breakage by reducing the number of components involved in rotation of the elongate flexible drive shaft. Further, direct translation of the rotational components can increase simplicity of the design and operation of the rotational atherectomy device. Cannulated motor 226 can provide the improved torque transmission during the rotation of the elongate flexible drive shaft.

The pump assembly 230 can include a pump 232 (or micropump), tubes 234, an external fitting 236, and a pump motor 238. Pump 232 can pump saline, or other fluids, to a distal portion of rotational atherectomy device 100. Pump 232 can be a peristaltic pump, a piezoelectric pump, an electromechanical integrated pump, a microdosing pump, a positive displacement pump, a quasi-peristaltic pump, or other micropump. Pump 232 can include one or more tubes 234 extend from, or extending through, pump 232 to pump saline from an exterior of housing 202 to a distal end of the rotational atherectomy device 100. In some embodiments, due to sterilization needs, it can be beneficial to use a pump with separation between the fluid and pump 232, such that the fluid only contacts tubes 234. External fitting 236 can couple to tube 234 and further couple to a tube external to housing 202. For example, external fitting 236 can be a luer fitting to couple a fluid bag (e.g., a saline bag). Pump 232 can be powered by pump motor 238, which can be controlled by controller assembly 240. Optionally, pump motor 238 can be a brushless DC motor. Pump motor 238 can allow pump 232 to operate at about 3.5 psi to about 4 psi, such that the fluid pumped by pump 232 prevents backflow of blood during the atherectomy procedure. Pump assembly 230 can include seals to prevent leakage into housing 202.

Figure 5:
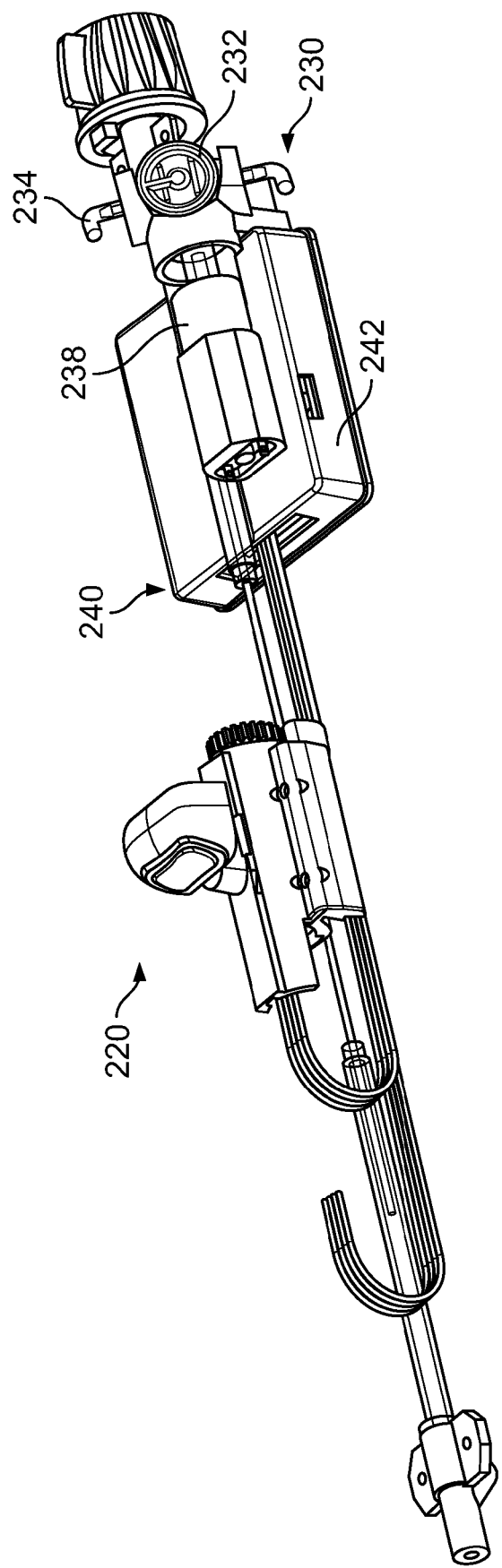
FIGS. 5, 6, and 7A-7B are perspective views of an interior of the handle assembly of FIG. 2 in accordance with some embodiments.
Figure 6:
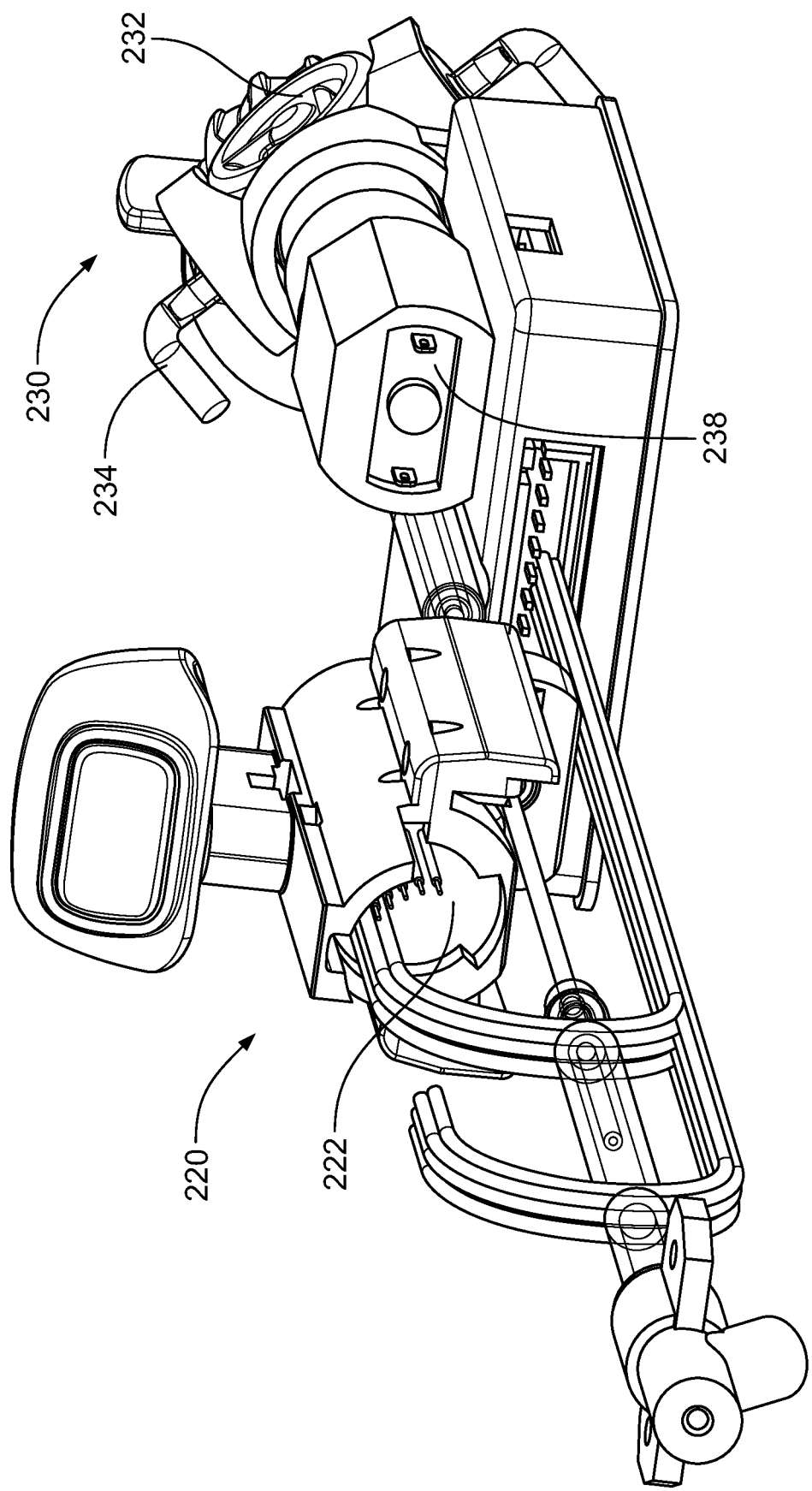

The controller assembly 240 can include a housing 242, and a controller 244. Housing 242 can provide a seal and barrier between controller 244 and the other components of handle assembly 200 to protect the controller 244 from liquid (e.g., blood from a patient, fluid from the pump 232). In some embodiments, the housing 242 can also provide a structural support for the pump assembly 230, as shown in FIGS. 5-7. The controller 244 can be electrically coupled to the components of the user controls 216 and control function of the components.

For example, the controller 244 can cause motor 222 to run or stop based on electrical motor switch 206, such that when electrical motor switch 206 is depressed, controller 244 causes motor 222 to run. In addition, controller 244 can determine and control a speed for rotating the drive shaft 136, and supply the appropriate power to the motor 222 based on user input via electrical switches 210a and/or 210b. For example, the rotational speed can be selected through a range of speeds with electrical switch 210a causing an increase in speed and electrical switch 210b causing a decrease in speed. In some embodiments, rotational speed is changed incrementally between a plurality of preset speeds. As such, a single depression of electrical switch 210a or 210b can cause controller 244 to increase current supplied to the motor 222 to cause an incremental change in speed. In some embodiments, depression of the electrical switch 210a or 210b will cause controller 244 to supply a current to cause a change in speed corresponding to a length of time that the electrical switch 210a or 210b is depressed. In another embodiment, the electrical switch 210a will cause controller 244 to determine a selection of a "high" rotational speed was made and provide the appropriate current, and the electrical switch 210b will cause controller 244 to determine a selection of a "low" rotational speed, in comparison to the high rotational speed, was made and provide the appropriate current. Additionally, controller 244 can control the light indicators associated with electrical switches 210a and 210b, as described above.

In some embodiments, the controller 244 can monitor and control a parameter, such as an amount of current supplied to the motor 222. Such monitoring and controlling features can provide a safety (shut-off) feature to the rotational atherectomy system 100 that prevents damage from occurring to the system 100 and/or a patient during use. For example, in various embodiments, the controller 244 is configured such that the current supplied does not exceed a threshold current value (e.g., prevents a large amount of current from being supplied to motor 222). Thus, the controller 244 can be programmed to provide current to the motor 222, but at a current level that is no greater than the threshold current value. The controller 244 can optionally limit the system 100 based exclusively on the current threshold value, in some embodiments, to provide an effective, yet simplified algorithm to the controller 244 as a safety feature.

The threshold current value can be a predetermined value that prevents irreversible damage or undesirable performance of the system 100 from occurring during use. For example, in some embodiments, the threshold current value is configured to limit the torque and/or speed of rotation of the system 100 such that the rotation of the elongate flexible drive shaft in a particular rotational direction (e.g., a first rotational direction) does not cause unwinding of the one or more filars of the elongate flexible drive shaft to occur. In some embodiments, the threshold current value is configured to limit the torque and/or speed of rotation of the system 100 such that the rotation of the elongate flexible drive shaft in a particular rotational direction (e.g., a first rotational direction) does not cause a change in a maximum diameter of the elongate flexible drive shaft to occur.

In some embodiments, if the current supplied reaches a threshold current value, the controller 244 can initiate a stopping protocol. For example, the stopping protocol can cause the controller 244 to reduce the amount of current supplied to the electrical motor to approximately zero. In some embodiments, such a reduction of current supplied can occur in a short period of time, substantially instantaneously, or over a longer period of time. In some embodiments, the stopping protocol can cause the controller 244 to reverse the direction of rotation of the motor 222, and therefore the rotation of the drive shaft 136. Such a reversal in direction of rotation of the drive shaft 136 can cause rotation of a distal end of the drive shaft to 136 to slow down or stop. The stopping protocol can aid in preventing motor 222 from burning out. In some cases, the stopping protocol is caused to a distal portion of drive shaft 136 being stuck in a vessel. Optionally, once rotation has begun, the stopping protocol can be executed after a predetermined amount of time (e.g., about 0.1 seconds to about 60 seconds). In some cases, the predetermined amount of time for executing the stopping protocol can be selected such that the predetermined amount of time begins when the current threshold is reached. For example, the drive shaft coil may begin to unwind once the current threshold is reached, and the controller may continue to provide current to the motor until the predetermined amount of time has passed. In some cases, the drive shaft coil may begin to unwind before the current threshold is reached, and the controller will continue to motor the current supplied and initiate the stopping protocol after the current threshold is reached.

Optionally, controller 244 can cause pump motor 238 to run or stop pump 232 based on depression of electrical pump switch 212. In some cases, a first depression of the electrical pump switch 212 will turn the saline pump on, while a second depression will turn the saline pump on. In some embodiments, the controller 244 control the light indicator associated with electrical pump switch 212, such that when the pump is on, a light is illuminated to inform the clinician that the pump is on.

In some embodiments, controller 244 can monitor guidewire detention mechanism 208 (e.g., via a sensor), such that controller 244 can determine when guidewire detention mechanism 208 is actuated (e.g., rotated) to releasably clamp and maintain the guidewire 134 in a stationary position relative to the handle assembly 200 (and, in turn, stationary in relation to rotations of the drive shaft 136 during an atherectomy treatment). In some embodiments, when the clinician is ready to begin the atherectomy treatment, the guidewire detention mechanism 208 can be actuated to releasably detain/lock the guidewire 134 in relation to the handle assembly 200. That way the guidewire 134 will not rotate while the drive shaft 136 is rotating, and the guidewire 134 will not translate while the carriage assembly 204 is being manually translated. Accordingly, controller 244 can prevent motor 222 from rotating the drive shaft 136 unless controller 244 detects that the guidewire detention mechanism 208 is actuated. Further, controller 244 can control illumination of the light indicator 214.

Optionally, the controller 244 can include a safety mechanism regarding operation of the handle assembly 200. For example, rotation of the drive shaft assembly 130 may be prohibited until the controller 244 detects that guidewire detention mechanism 208 is actuated, the pump has been turned on via electrical pump switch 212, and a rotation speed has been selected via electrical switch 210a or 210b. As another example, the controller 244 can selectively illuminate indicator lights associated with the electrical switch 210a or 210b, the electrical pump switch 212, and the guidewire detention mechanism 208 light indicator 214 to inform a clinician which systems are powered on. In some embodiments, a lack of three lights indicts to the clinician that the rotational atherectomy system 100 should not be operated, at least until all three systems (the motor, the pump, the guidewire lock) are lit. For example, each system may have a green light, such that three green lights indicates the clinician can proceed with the atherectomy procedure. Optionally, only the guidewire detection mechanism 208 needs to be actuated for the controller 244 to allow rotation of the rotational atherectomy system 100.

In some embodiments, the handle assembly 200 can also include a battery or other power source (not shown). The battery or power source may be integrated into the housing 202. For example, the battery could be disposable with handle assembly 200. In some embodiments, the power source could have an external component configured to make an electrical connection (e.g., plug into a wall socket) to provide power. Optionally, the battery could be reusable. For example, housing 202 can be configured to receive a rechargeable battery, either on an exterior portion of housing 202, or within interior cavity 201.

Figure 8:
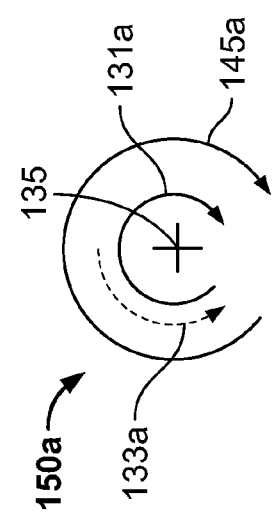
FIG. 8 is a schematic diagram representing an example drive shaft embodiment that includes filars that are wound in a direction opposite to a direction of a spiral path defined by multiple abrasive elements that are arranged at differing radial angles in accordance with some embodiments.

Referring to FIG. 8, a schematic diagram 150a depicting an end view of the drive shaft 136 (looking distally) with the abrasive elements 138 can be used to illustrate the filar spiral wind direction 131a (of the drive shaft 136) in comparison to the spiral path defined by the abrasive element centers of mass 133a (of the abrasive elements 138 of FIG. 10, and the abrasive elements 144a-e of FIG. 11), and also in comparison to the rotation direction 145a of the drive shaft 136 during use. In the depicted embodiment, the filar spiral wind direction 131a is clockwise around the central longitudinal axis 135 of the drive shaft 136. Also, the rotation direction 145a of the drive shaft 136 during use is clockwise around the central longitudinal axis 135 of the drive shaft 136. In contrast, the spiral path defined by the abrasive element centers of mass 133a is counterclockwise around the central longitudinal axis 135 of the drive shaft 136. In other words, the filar spiral wind direction 131a and the rotation direction 145a of the drive shaft 136 during use are the same direction, whereas the spiral path defined by the abrasive element centers of mass 133a is the opposite direction of: (i) the filar spiral wind direction 131a and (ii) the opposite direction of the rotation direction 145a of the drive shaft 136 during use.

Figure 9:
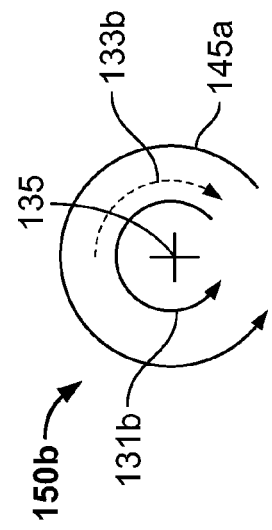
FIG. 9 is a schematic diagram representing another example drive shaft embodiment that includes filars that are wound in a direction opposite to the direction of a spiral path defined by multiple abrasive elements that are arranged at differing radial angles in accordance with some embodiments.

Referring also to FIG. 9, another schematic diagram 150b depicting an end view of the drive shaft 136 (looking distally) with the abrasive elements 144a-e (as shown in FIG. 11) can be used to illustrate another arrangement of the filar spiral wind direction 131b (of the drive shaft 136) in comparison to the spiral path defined by the abrasive element centers of mass 133b (of the abrasive elements 144a-e), and also in comparison to the rotation direction 145b of the drive shaft 136 during use. In the depicted embodiment, the filar spiral wind direction 131b is counterclockwise around the central longitudinal axis 135 of the drive shaft 136. Also, the rotation direction 145*b* of the drive shaft 136 during use is counterclockwise around the central longitudinal axis 135 of the drive shaft 136. In contrast, the spiral path defined by the abrasive element centers of mass 133*b* is clockwise around the central longitudinal axis 135 of the drive shaft 136. In other words, here again in this example, the filar spiral wind direction 131*b* and the rotation direction 145*b* of the drive shaft 136 during use are the same direction, whereas the spiral path defined by the abrasive element centers of mass 133*b* is the opposite direction of: (i) the filar spiral wind direction 131*b* and (ii) the opposite direction of the rotation direction 145*b* of the drive shaft 136 during use.

The relative arrangements between: (i) the filar spiral wind direction 131*a* or 131*b*, (ii) the spiral path defined by the abrasive element centers of mass 133*a* or 133*b*, and (iii) the rotation direction 145*a* or 145*b* of the drive shaft 136 during use, as described above in reference to FIGS. 9 and 10, provide particular operational advantages in some usage scenarios. For example, when the direction of rotation and the direction the filars are wound are the same direction, the winds of the filars will tend to radially expand (the drive shaft 136 will tend to "open up," as shown in FIGS. 10 and 11), resulting in less friction, little to no need for lubrication, less stress induced on the guidewire, and so on. Additionally, when the direction of rotation of the drive shaft 136 and the direction of the spiral path defined by the centers of mass of the abrasive elements 144 are opposite, such an arrangement can advantageously provide a smoother running and more controllable atherectomy procedure as compared to systems that rotate the drive shaft in the same direction as the spiral path defined by the centers of mass of the abrasive elements. For example, rather than causing the abrasive elements 144 to corkscrew into the stenotic lesion material (as can occur when the drive shaft rotational direction is the same as the direction of the spiral path defined by the centers of mass of the abrasive elements), the abrasive elements 144 can instead abrade the stenotic lesion material in more of a gradual, smooth, and controllable manner.

Referring to FIG. 10, a distal end portion of the drive shaft 136 is shown in a longitudinal cross-sectional view. The distal end portion of the drive shaft 136 includes the one or more abrasive elements 138 that are eccentrically-fixed to the driveshaft 136, the optional distal stability element 140 with an abrasive outer surface, and the distal drive shaft extension portion 142.

In the depicted embodiment, the one or more abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating.

In the depicted embodiment, the two outermost abrasive elements of the abrasive elements 138 are smaller in maximum diameter than the three inner abrasive elements of the abrasive elements 138. In some embodiments, all of the abrasive elements are the same size. In particular embodiments, three or more different sizes of abrasive elements are included. Any and all such possible arrangements of sizes of abrasive elements are envisioned and within the scope of this disclosure.

The one or more abrasive elements 138 can be made to any suitable size. For clarity, the size of the one or more abrasive elements 138 will refer herein to the maximum outer diameter of individual abrasive elements of the one or more abrasive elements 138. In some embodiments, the one or more abrasive elements 138 are about 2 mm in size (maximum outer diameter). In some embodiments, the size of the one or more abrasive elements 138 is in a range of about 1.5 mm to about 2.5 mm, or about 1.0 mm to about 3.0 mm, or about 0.5 mm to about 4.0 mm, without limitation. Again, in a single embodiment, one or more of the abrasive elements 138 can have a different size in comparison to the other abrasive elements 138. In some embodiments, the two outermost abrasive elements are about 1.5 mm in diameter and the inner abrasive elements are about 2.0 mm in diameter.

In the depicted embodiment, the one or more abrasive elements 138, individually, are oblong in shape. A variety of different shapes can be used for the one or more abrasive elements 138. For example, in some embodiments the one or more abrasive elements 138 are individually shaped as spheres, discs, rods, cylinders, polyhedrons, cubes, prisms, and the like. In some embodiments, such as the depicted embodiment, all of the one or more abrasive elements 138 are the same shape. In particular embodiments, one or more of the abrasive elements 138 has a different shape than one or more of the other abrasive elements 138. That is, two, three, or more differing shapes of individual abrasive elements 138 can be combined on the same drive shaft 136.

In the depicted embodiment, adjacent abrasive elements of the one or more abrasive elements 138 are spaced apart from each other. For example, in the depicted embodiment the two distal-most individual abrasive elements are spaced apart from each other by a distance 'X'. In some embodiments, the spacing between adjacent abrasive elements is consistent between all of the one or more abrasive elements 138. Alternatively, in some embodiments the spacing between some adjacent pairs of abrasive elements differs from the spacing between other adjacent pairs of abrasive elements.

In some embodiments, the spacing distance X in ratio to the maximum diameter of the abrasive elements 138 is about 1:1. That is, the spacing distance X is about equal to the maximum diameter. The spacing distance X can be selected to provide a desired degree of flexibility of the portion of the drive shaft 136 to which the one or more abrasive elements 138 are attached. In some embodiments, the ratio is about 1.5:1 (i.e., X is about 1.5 times longer than the maximum diameter). In some embodiments, the ratio is in a range of about 0.2:1 to about 0.4:1, or about 0.4:1 to about 0.6:1, or about 0.6:1 to about 0.8:1, or about 0.8:1 to about 1:1, or about 1:1 to about 1.2:1, or about 1.2:1 to about 1.4:1, or about 1.4:1 to about 1.6:1, or about 1.6:1 to about 1.8:1, or about 1.8:1 to about 2.0:1, or about 2.0:1 to about 2.2:1, or about 2.2:1 to about 2.4:1, or about 2.4:1 to about 3.0:1, or about 3.0:1 to about 4.0:1, and anywhere between or beyond those ranges.

In the depicted embodiment, the center of mass of each one of the one or more abrasive elements 138 is offset from the longitudinal axis of the drive shaft 136 along a same radial angle. Said another way, the centers of mass of all of the one or more abrasive elements 138 are coplanar with the longitudinal axis of the drive shaft 136. If the size of each of the one or more abrasive elements 138 is equal, the centers of mass of the one or more abrasive elements 138 would be collinear on a line that is parallel to the longitudinal axis of the drive shaft 136.

Referring to FIG. 11, according to some embodiments of the rotational atherectomy devices provided herein, one or more abrasive elements 144 are arranged at differing radial angles in relation to the drive shaft 136 as depicted here. Further, the draft shaft 136 is shown as in an unwinding state, as unwinding may optionally occur during rotation of the drive shaft 136 in some embodiments. In such a case, a path defined by the centers of mass of the one or more abrasive elements 144 spirals along the drive shaft 136 around the central longitudinal axis of the drive shaft 136. In some cases (e.g., when the diameters of the one or more abrasive elements 144 are equal and the adjacent abrasive elements are all equally spaced), the centers of mass of the one or more abrasive elements 144 define a helical path along/around the drive shaft 136. It has been found that such arrangements can provide a desirably-shaped orbital rotation of the one or more abrasive elements 144. It should be noted that, in some embodiments, a controller assembly (e.g., controller assembly 240) is configured to control rotation and current input such that the drive shaft 136 is prevented from unwinding during rotation of the drive shaft 136.

It should be understood that any of the structural features described in the context of one embodiment of the rotational atherectomy devices provided herein can be combined with any of the structural features described in the context of one or more other embodiments of the rotational atherectomy devices provided herein. For example, the size, spacing, and/or shape features (and any other characteristics) of the one or more abrasive elements 138 described in the context of FIG. 1 can be incorporated in any desired combination with the spiral arrangement of the one or more abrasive elements 144.

In some embodiments, the drive shaft assembly 130 includes at least four abrasive elements 144 attached to a distal end portion of the drive shaft 136 and each has a center of mass offset from the longitudinal axis of the drive shaft 136. A spiral path defined by connecting the centers of mass of the at least four abrasive elements 144 spirals around the longitudinal axis of the drive shaft 136. An overall radial angle of the spiral path is defined by a radial angle between a distal-most abrasive element of the at least four abrasive elements 144 and a proximal-most abrasive element of the at least four abrasive elements 144. In some embodiments, the overall radial angle of the spiral path of the at least four abrasive elements 144 is always less than 180 degrees along any 10 cm length of the distal end portion of the drive shaft 136. In some embodiments, the overall radial angle of the spiral path of the at least four abrasive elements 144 is always less than 170 degrees, or less than 160 degrees, or less than 150 degrees, or less than 140 degrees, or less than 130 degrees, or less than 120 degrees, or less than 110 degrees, or less than 100 degrees, or less than 90 degrees along any 10 cm length of the distal end portion of the drive shaft 136.

In some embodiments, such as the depicted embodiment, the drive shaft assembly 130 includes a concentric abrasive tip member 141. The concentric abrasive tip member 141 can be affixed to, and extending distally from, a distal-most end of the drive shaft 136. In some embodiments that include the concentric abrasive tip member 141, no distal stability element is included 140. In particular embodiments (such as the depicted embodiment), the concentric abrasive tip member 141 and the distal stability element are both included 140.

In some embodiments the concentric abrasive tip member 141 may be made of metallic materials such as stainless steel, tungsten, molybdenum, iridium, cobalt, cadmium, and the like, and alloys thereof. The concentric abrasive tip member 141 has a fixed outer diameter. That is, the concentric abrasive tip member 141 is not an expandable member in the depicted embodiment. The concentric abrasive tip member 141 may be mounted to the filars of the drive shaft 136 using a biocompatible adhesive, by welding, by press fitting, and the like, and by combinations thereof. Alternatively, the concentric abrasive tip member 141 can be integrally formed as a unitary structure with the filars of the drive shaft 136 (e.g., using filars of a different size or density, using filars that are double-wound to provide multiple filar layers, or the like).

In some embodiments, the concentric abrasive tip member 141 has an abrasive coating on its exterior surface. In particular embodiments, the concentric abrasive tip member 141 includes an abrasive material along an exterior circumferential surface, or on a distal end face/surface, or both. For example, in some embodiments a diamond coating (or other suitable type of abrasive coating) is disposed on the outer surface of the concentric abrasive tip member 141. In some cases, such an abrasive surface on the concentric abrasive tip member 141 can help facilitate the passage of the concentric abrasive tip member 141 through vessel restrictions (such as calcified areas of a blood vessel).

In some embodiments, the concentric abrasive tip member 141 has an exterior surface that is smoother and different from an abrasive exterior surface of the one or more abrasive elements 138. That may be the case whether or not the concentric abrasive tip member 141 have an abrasive coating on its exterior surface. In some embodiments, the abrasive coating on the exterior surface of the concentric abrasive tip member 141 is rougher than the abrasive surfaces on the one or more abrasive elements 138.

The maximum outer diameter of the concentric abrasive tip member 141 may be smaller than, equal to, or larger than the outer diameter of the adjacent portion of the drive shaft 136. The maximum outer diameter of the concentric abrasive tip member 141 may be smaller than, equal to, or larger than the maximum outer diameter of each of the one or more abrasive elements 144a-e. The lateral width of the concentric abrasive tip member 141 (e.g., measured parallel to the longitudinal axis of the drive shaft 136) may be smaller than, equal to, or larger than the maximum lateral width of each of the one or more abrasive elements 144a-e.

The concentric abrasive tip member 141 defines a central opening that is coaxial with the lumen defined by the drive shaft 136. Accordingly, a guidewire (e.g., the guidewire 134 of FIG. 1) can extend through the concentric abrasive tip member 141. In some embodiments, the concentric abrasive tip member 141 is shaped as a toroid. In particular embodiments, the concentric abrasive tip member 141 is shaped as a hollow cylinder. In certain embodiments, the outer surface of the concentric abrasive tip member 141 defines one or more grooves, teeth, edges, and the like, and combinations thereof.

Figure 12:
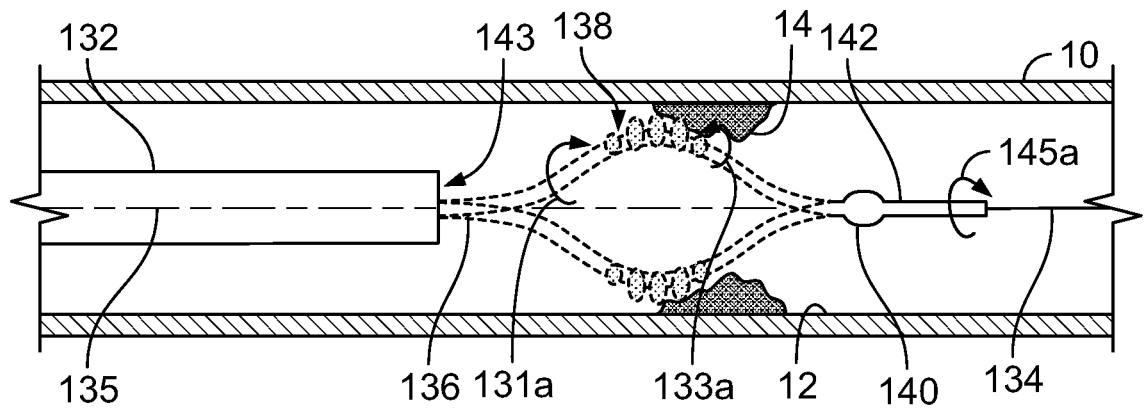
FIG. 12 shows the example rotational atherectomy device of FIGS. 10 or 11 in use at a first longitudinal position in the region of the lesion. A multi-portion abrasive element of the rotational atherectomy device is being rotated along an orbital path to abrade the lesion.
Figure 13:
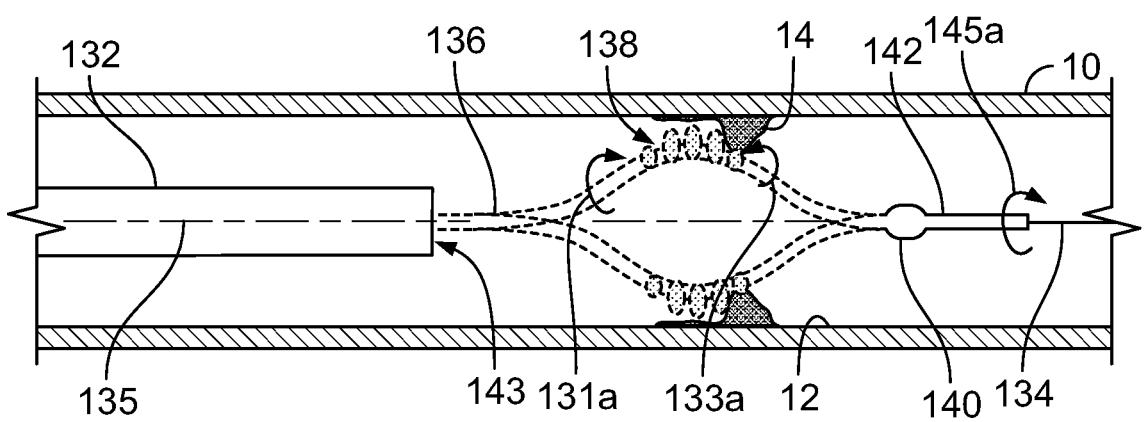
FIG. 13 shows the rotational atherectomy device of FIGS. 10 or 11 with the abrasive element being rotated at a second longitudinal position that is distal of the first longitudinal position.
Figure 14:
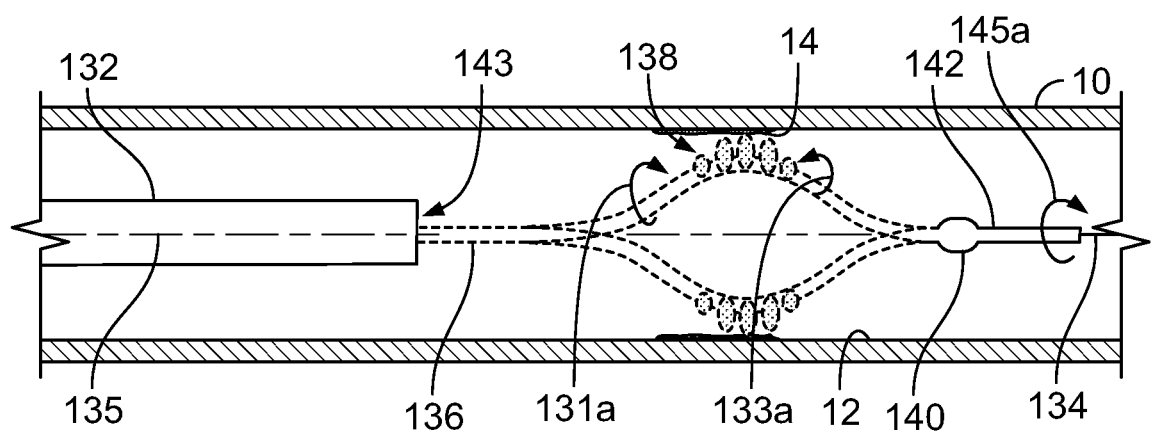
FIG. 14 shows the rotational atherectomy device of FIGS. 10 or 11 with the abrasive element being rotated at a third longitudinal position that is distal of the second longitudinal position.

Next, as depicted by FIGS. 12-14, the rotation and translational motions of the drive shaft 136 (and the one or more abrasive elements 138) can be commenced to perform ablation of the lesion 14.

In some implementations, prior to the ablation of the lesion 14 by the one or more abrasive elements 138, an inflatable member can be used as an angioplasty balloon to treat the lesion 14. That is, an inflatable member (on the sheath 132, for example) can be positioned within the lesion 14 and then inflated to compress the lesion 14 against the inner wall 12 of the vessel 10. Thereafter, the rotational atherectomy procedure can be performed. In some implementations, such an inflatable member can be used as an angioplasty balloon after the rotational atherectomy procedure is performed. In some implementations, additionally or alternatively, a stent can be placed at lesion 14 using an inflatable member on the sheath 132 (or another balloon member associated with the drive shaft assembly 130) after the rotational atherectomy procedure is performed.

The guidewire 134 may remain extending from the distal end of the drive shaft 136 during the atherectomy procedure as shown. For example, as depicted by FIGS. 12-14, the guidewire 134 extends through the lumen of the drive shaft 136 and further extends distally of the distal end of the distal extension portion 142 during the rotation and translational motions of the drive shaft 136 (refer, for example, to FIGS. 12-14). In some alternative implementations, the guidewire 134 is withdrawn completely out of the lumen of the drive shaft 136 prior to during the rotation and translational motions of the drive shaft 136 for abrading the lesion 14. In other implementations, the guidewire is withdrawn only partially. That is, in some implementations a portion of the guidewire remains within the lumen of the drive shaft 136 during rotation of the drive shaft 136, but remains only in a proximal portion that is not subject to the significant orbital path in the area of the one or more abrasive elements 138 (e.g., remains within the portion of the drive shaft 136 that remains in the sheath 132).

To perform the atherectomy procedure, the drive shaft 136 is rotated at a high rate of rotation (e.g., 20,000-160,000 rpm) such that the eccentric one or more abrasive elements 138 revolve in an orbital path about an axis of rotation and thereby contacts and removes portions of the lesion 14.

Still referring to FIGS. 12-14, the rotational atherectomy system 100 is depicted during the high-speed rotation of the drive shaft 136. The centrifugal force acting on the eccentrically weighted one or more abrasive elements 138 causes the one or more abrasive elements 138 to orbit in an orbital path 131a around the axis of rotation 135. In some implementations, the orbital path can be somewhat similar to the orbital motion of a "jump rope." As shown, some portions of the drive shaft 136 (e.g., a portion that is just distal of the sheath 132 and another portion that is distal of the distal stability element 140) can remain in general alignment with the axis of rotation 135, but the particular portion of the drive shaft 136 adjacent to the one or more abrasive elements 138 is not aligned with the axis of rotation 135 (and instead orbits around the axis 135). As such, in some implementations, the axis of rotation 135 may be aligned with the longitudinal axis of a proximal part of the drive shaft 136 (e.g., a part within the distal end of the sheath 132) and with the longitudinal axis of the distal extension portion 142 of the drive shaft 136.

In some implementations, as the one or more abrasive elements 138 rotates, the clinician operator slowly advances the carriage assembly 204 distally (and, optionally, reciprocates both distally and proximally) in a longitudinal translation direction so that the abrasive surface of the one or more abrasive elements 138 scrapes against additional portions of the occluding lesion 14 to reduce the size of the occlusion, and to thereby improve the blood flow through the vessel 10. This combination of rotational and translational motion of the one or more abrasive elements 138 is depicted by the sequence of FIGS. 12-14.

In some embodiments, the sheath 132 may define one or more lumens (e.g., the same lumen as, or another lumen than, the lumen in which the drive shaft 136 is located) that can be used for aspiration (e.g., of abraded particles of the lesion 14). In some cases, such lumens can be additionally or alternatively used to deliver perfusion and/or therapeutic substances to the location of the lesion 14, or to prevent backflow of blood from vessel 10 into sheath 132.

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:

1. A rotational atherectomy device, comprising:
   a torque-transmitting coil slidably and rotatably disposed within a lumen of a sheath such that a distal end portion of the torque-transmitting coil is positioned distally of a distal end of the sheath;
   an eccentric abrasive element fixedly mounted to the distal end portion of the torque-transmitting coil; and
   a rotational atherectomy control handle, including:
      an outer handle housing having a front portion connected with a proximal end of the sheath and a rear portion, the outer handle housing surrounding both an electric motor to drive rotation of the torque-transmitting coil and a controller assembly that regulates a rotational speed of the torque-transmitting coil and that activates the electric motor to rotate the torque-transmitting coil in response to actuation of an atherectomy trigger button;
      a carriage arranged within the outer handle housing and being movable in a longitudinal direction relative to the outer handle housing so as to longitudinally translate the torque-transmitting coil relative to the sheath, the carriage carrying the atherectomy trigger button external to the outer handle housing and the electric motor within the outer handle housing;
      a rear guidewire port accessible along the rear portion of the outer handle housing;
      a guidewire brake actuator disposed along the rear portion of the outer handle housing and being movable relative to the outer handle housing to a locked position to releasably lock a guidewire in a stationary position relative to the outer handle housing; and
      a user interface accessible along an upper exterior face of the outer handle housing and including: the atherectomy trigger button movable relative to the outer handle housing and being in communication with the controller assembly housed within the outer handle housing, a plurality of rotation speed control buttons positioned rearward of the atherectomy trigger button for input of a selected rotational speed setting for the torque-transmitting coil, and a guidewire brake light indicator that illuminates in response to movement of the guidewire brake actuator to the locked position and is positioned between a rearmost one of the plurality of rotation speed control buttons and the guidewire brake actuator,
      wherein the controller assembly housed within the outer handle housing is configured to prevent activation of the electric motor in response to detecting that the guidewire brake actuator is moved to an unlocked position.

2. The rotational atherectomy device of claim 1, wherein rotational atherectomy control handle further comprises a gear assembly housed within the outer handle housing and carried by the carriage, the gear assembly being connected to the electric motor and being coupled with the torque-transmitting coil so that the electric motor drives rotation of the torque-transmitting coil.

3. The rotational atherectomy device of claim 1, further comprising the guidewire.

4. The rotational atherectomy device of claim 3, wherein the guidewire is configured to be slidably received through a central lumen of the torque-transmitting coil and through the rotational atherectomy control handle such that a distal portion of the guidewire extends distally of the torque-transmitting coil and a proximal portion of the guidewire extends through the rear guidewire port accessible along the rear portion of the outer handle housing.

5. The rotational atherectomy device of claim 1, wherein the controller assembly housed within the outer handle housing is configured to monitor the guidewire brake actuator via a sensor so as to activate the guidewire brake light indicator in response to the guidewire brake actuator being moved to releasably lock the guidewire in the stationary position relative to the outer handle housing.

6. The rotational atherectomy device of claim 1, wherein the controller assembly housed within the outer handle housing is configured to monitor an amount of current supplied to the electric motor and to limit the amount of current supplied to the electric motor such that the amount of current does not exceed a threshold current value.

7. The rotational atherectomy device of claim 6, wherein the controller assembly housed within the outer handle housing is configured to control rotation of the electric motor by initiating a stopping protocol when the amount of the current supplied reaches the threshold current value.

8. The rotational atherectomy device of claim 7, wherein the stopping protocol comprises reversing rotation of the torque-transmitting coil by reversing the rotation caused by the electrical motor from a first rotational direction to a second rotational direction.

9. The rotational atherectomy device of claim 1, wherein at least one of the rotation speed control buttons positioned along the outer handling housing is configured to emit a light indicative of the selected rotational speed setting.

10. The rotational atherectomy device of claim 1, further comprising a fluid fitting extending from the outer handle housing for connection with a saline source.

11. The rotational atherectomy device of claim 10, wherein the rotational atherectomy control handle defines a longitudinal access aligned with a central longitudinal axis of the torque-transmitting coil, and wherein the fluid fitting is connected to the outer handle housing at a location laterally offset from the central longitudinal axis of the rotational atherectomy control handle.

12. The rotational atherectomy device of claim 11, wherein the electric motor is positioned within the outer handle housing in an orientation laterally offset from the longitudinal axis of the rotational atherectomy control handle.

13. The rotational atherectomy device of claim 1, wherein the user interface accessible along the upper exterior face of the outer handle housing further includes a fluid delivery button positioned rearward of the plurality of rotation speed control buttons and being configured to initiate delivery of fluid through the sheath.

14. The rotational atherectomy device of claim 13, wherein the rotational atherectomy control handle further comprises a pump housed within the outer handle housing.

15. The rotational atherectomy device of claim 14, wherein the pump housed within the outer handle housing is configured to deliver a flush fluid into the sheath and toward to the distal end portion of the torque-transmitting coil.

16. The rotational atherectomy device of claim 1, wherein the eccentric abrasive element comprises a first eccentric abrasive element, further comprising at least a second eccentric abrasive element spaced distally apart from the first eccentric abrasive element along the torque-transmitting coil.

17. The rotational atherectomy device of claim 16, further comprising a third eccentric abrasive element spaced distally apart from the second eccentric abrasive element along the torque-transmitting coil, wherein the first, second, and third eccentric abrasive elements are offset from a longitudinal axis of the torque-transmitting coil at differing radial angles relative to one another.

18. The rotational atherectomy device of claim 1, wherein the eccentric abrasive element comprises a diamond-coated metallic burr having a maximum outer diameter of about 2 mm.

19. A rotational atherectomy device, comprising:
a torque-transmitting coil slidably and rotatably disposed within a lumen of a sheath such that a distal end portion of the torque-transmitting coil is positioned distally of a distal end of the sheath;
an eccentric abrasive element fixedly mounted to the distal end portion of the torque-transmitting coil; and
a rotational atherectomy control handle, including:
an outer handle housing having a front portion connected with a proximal end of the sheath and a rear portion, the outer handle housing surrounding both an electric motor to drive rotation of the torque-transmitting coil and a controller assembly that regulates a rotational speed of the torque-transmitting coil and that activates the electric motor to rotate the torque-transmitting coil in response to actuation of an atherectomy trigger button;
a carriage arranged within the outer handle housing and being movable in a longitudinal direction relative to the outer handle housing so as to longitudinally translate the torque-transmitting coil relative to the sheath, the carriage carrying the atherectomy trigger button external to the outer handle housing and the electric motor within the outer handle housing;
a rear guidewire port accessible along the rear portion of the outer handle housing;
a guidewire brake actuator disposed along the rear portion of the outer handle housing and being movable relative to the outer handle housing to a locked position to releasably lock a guidewire in a stationary position relative to the outer handle housing; and
a user interface accessible along an upper exterior face of the outer handle housing and including: the atherectomy trigger button movable relative to the outer handle housing and being in communication with the controller assembly housed within the outer handle housing, a plurality of rotation speed control buttons positioned rearward of the atherectomy trigger button for input of a selected rotational speed setting for the torque-transmitting coil, and a guidewire brake light indicator that illuminates in response to movement of the guidewire brake actuator to the locked position and is positioned between a rearmost one of the plurality of rotation speed control buttons and the guidewire brake actuator, and
a gear assembly housed within the outer handle housing and carried by the carriage, the gear assembly being connected to the electric motor and being coupled with the torque-transmitting coil so that the electric motor drives rotation of the torque-transmitting coil,
wherein the torque-transmitting coil has an exterior coil diameter defined by one or more filars helically wound in a filar wind direction, and wherein the electric motor is configured to drive rotation of the torque-transmitting coil in a first rotational direction that is the same as the filar wind direction, and
wherein responsive to detecting that the guidewire brake actuator is moved to an unlocked position, the controller assembly housed within the outer handle housing is configured to prevent the electric motor from driving rotation of the torque-transmitting coil for rotational atherectomy.

* * * * *